United States Patent
Singhal et al.

(10) Patent No.: US 11,933,783 B2
(45) Date of Patent: Mar. 19, 2024

(54) LIQUID BIOPSY YIELD ENHANCEMENT

(71) Applicants: Seema Singhal, Chicago, IL (US); Jayesh Mehta, Chicago, IL (US); Neil Mehta, Philadelphia, PA (US); Aran Mehta, Chicago, IL (US)

(72) Inventors: Seema Singhal, Chicago, IL (US); Jayesh Mehta, Chicago, IL (US); Neil Mehta, Philadelphia, PA (US); Aran Mehta, Chicago, IL (US)

(*) Notice: Subject to any disclaimer, the term of this patent is extended or adjusted under 35 U.S.C. 154(b) by 528 days.

(21) Appl. No.: 16/932,989

(22) Filed: Jul. 20, 2020

(65) Prior Publication Data
US 2021/0263032 A1 Aug. 26, 2021

Related U.S. Application Data

(60) Provisional application No. 62/981,326, filed on Feb. 25, 2020.

(51) Int. Cl.
*G01N 33/574* (2006.01)
*A61K 45/06* (2006.01)

(52) U.S. Cl.
CPC .......... *G01N 33/574* (2013.01); *A61K 45/06* (2013.01); *G01N 2333/71* (2013.01); *G01N 2333/715* (2013.01)

(58) Field of Classification Search
CPC ............. G01N 33/5005; G01N 33/574; G01N 2333/71; G01N 2333/715
See application file for complete search history.

(56) References Cited

U.S. PATENT DOCUMENTS

2018/0140664 A1  5/2018  van Dongen et al.
2018/0305766 A1  10/2018  Ghobrial et al.

FOREIGN PATENT DOCUMENTS

WO  WO-2009/064933 A2  5/2009
WO  WO-2015/061091 A1  4/2015
WO  WO-2017/198879 A1  11/2017

OTHER PUBLICATIONS

Domanska et al., Clin Exp Metastasis, 2014, 31:829-839.*
DiPersia et al., Biol Blood Marrow Transplant, 2011, 17:943-955.*
Waldschmidt et al., Semin Hematol. Jan. 2018, 55(1):33-37.*
Liu et al., PLos Comput. Biol. 2022: 18(4), e1009497: 1-23.*
Encoclopedia.com, Oxford University Press May 29, 2018.*
Price et al., Science Translation Medicine, 2016, 8(340): ra73:1-12.*
Xu et al., Drug Design, Development and Therapy, 2015, 9:4953-4964.*
Supplemental material of Price et al. (Science Translation Medicine, 2016, 8(340): ra73:1-12), 2016, 37 pages.*

Debnath B et al. Small molecule inhibitors of CXCR4. Theranostics 2013; 3(1):47-75.
Flores-Montero J et al. Next generation flow for highly sensitive and standardized detection of minimal residual disease in multiple myeloma. Leukemia 2017; 31(10):2094-103.
Fricker SP. Physiology and pharmacology of plerixafor. Transfus Med Hemother 2013; 40:237-45.
Kato Y et al. A new packing for separation of DNA restriction fragments by high performance liquid chromatography. J Biochem 1984; 95(1):83-86.
Kumar S et al. International Myeloma Working Group consensus criteria for response and minimal residual disease assessment in multiple myeloma. Lancet Oncol 2016; 17:e328-46.
Harouaka RA et al. Circulating tumor cell enrichment based on physical properties. J Lab Autom 2013; 18(6):455-68.
Huber CG et al. High-resolution liquid chromatography of DNA fragments on non-porous poly(styrene-divinylbenzene) particles. Nucleic Acids Res 1993; 21(5):1061-66.
Landgren O et al. New developments in diagnosis, prognosis, and assessment of response in multiple myeloma. Clin Cancer Res 2016; 22:5428-33.
Lapierre V et al. Ancestim (r-metHuSCF) plus filgrastim and/or chemotherapy for mobilization of blood progenitors in 513 poorly mobilizing cancer patients: the French compassionate experience. Bone Marrow Transplant 2011; 46(7):936-42.
Liu MC et al. Genome-wide cell-free DNA (cfDNA) methylation signatures and effect on tissue of origin (TOO) performance. J Clin Oncol 2019; 37 (suppl):3049.
Merker JD et al. Circulating tumor DNA analysis in patients with cancer: American Society of Clinical Oncology and College of American Pathologists joint review. J Clin Oncol 2018; 36:1631-41.
Mishima Y et al. The mutational landscape of circulating tumor cells in multiple myeloma. Cell Rep 2017; 19(1):218-24.
Mithraprabhu S et al. Circulating tumour DNA analysis demonstrates spatial mutational heterogeneity that coincides with disease relapse in myeloma. Leukemia 2017; 31(8):1695-705.
Pantel K et al. Liquid biopsy and minimal residual disease—latest advances and implications for cure. Nat Rev Clin Oncol 2019; 16:409-24.
Rajkumar SV et al. International Myeloma Working Group updated criteria for the diagnosis of multiple myeloma. Lancet Oncol. 2014; 15(12):e538-48.
Rasche L et al. Spatial genomic heterogeneity in multiple myeloma revealed by multi-region sequencing. Nat Commun 2017; 8(1):268.
Singhal S et al. The relationship between the serum free light chain assay and serum immunofixation electrophoresis, and the definition of concordant and discordant free light chain ratios. Blood 2009; 114(1):38-39.
Waldschmidt JM et al. Comprehensive characterization of circulating and bone marrow-derived multiple myeloma cells at minimal residual disease. Semin Hematol 2018; 55:33-37.
Zhao H et al. CXCR4 over-expression and survival in cancer: a system review and meta-analysis. Oncotarget 2015; 6(7):5022-40.

(Continued)

*Primary Examiner* — Hong Sang
(74) *Attorney, Agent, or Firm* — Goodwin Procter LLP

(57) ABSTRACT

Provided herein are methods, kits, systems, and compositions or liquid biopsy yield enhancement.

30 Claims, 1 Drawing Sheet

(56) References Cited

OTHER PUBLICATIONS

Fruehauf S et al. Mobilization of peripheral blood stem cells for autologous transplant in non-Hodgkin's lymphoma and multiple myeloma patients by plerixafor and G-CSF and detection of tumor cell mobilization by PCR in multiple myeloma patients. Bone Marrow Transplant 2010; 45(2):269-75.

International Search Report and Written Opinion for PCT/US2020/042786, dated Oct. 21, 2020.

* cited by examiner

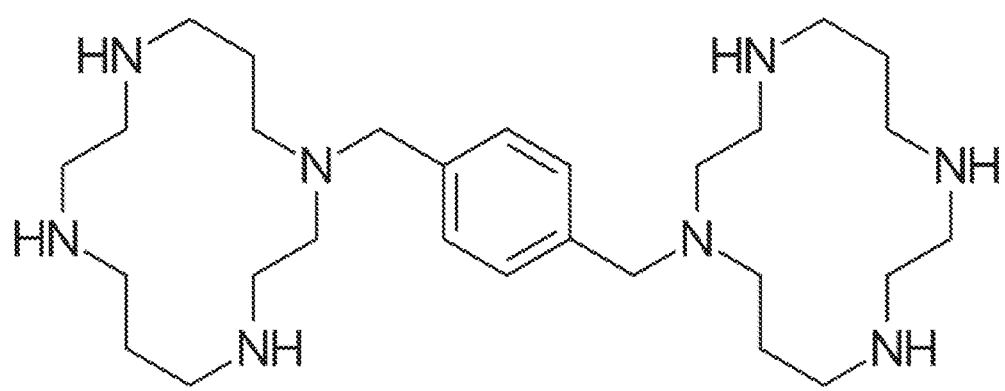

LIQUID BIOPSY YIELD ENHANCEMENT

CROSS REFERENCE TO RELATED APPLICATIONS

This application claims the benefit of, and priority to, U.S. Provisional Application No. 62/981,326, filed on Feb. 25, 2020, the content of which is hereby incorporated by reference in its entirety.

BACKGROUND OF THE INVENTION

Disease detection, diagnostic, and prognostic methods often rely on sampling of diseased cells, e.g., cancer cells. In many cases, tissue biopsies to obtain such cells can be invasive and painful, and carry risks of surgical complications. For example, in particular cases, such as multiple myeloma, cancerous cells are obtained via a puncture of the bone (bone marrow biopsy), a procedure that is extremely unpleasant for patients. In many cases, access to such diseased tissue is difficult, further complicating sampling of diseased cells for accurate diagnosis.

In some cases, distribution of the diseased cells within the patient is patchy, further complicating biopsy and diagnosis.

A considerable number of patients with seemingly successful cancer treatment, e.g., complete tumor resection or exhibiting complete remission (CR) after treatment suffer relapse within a variable period of time. Landgren et al., New developments in diagnosis, prognosis, and assessment of response in multiple myeloma, Clin Cancer Res 2016; 22:5428-33, which is hereby incorporated by reference in its entirety. Such relapses demonstrate the presence of undetected micrometastases or minimal residual disease (MRD) even after seemingly successful therapy. Presence of MRD is predictive of relapse (relapse signifying presence of disease that is detectable by conventional techniques) and is an important prognostic factor in several malignancies. Pantel K et al. Liquid biopsy and minimal residual disease—latest advances and implications for cure, Nat Rev Clin Oncol 2019; 16:409-24, which is hereby incorporated by reference in its entirety. Indeed, a major practical application of MRD detection is the administration of cancer therapy in a subject if MRD is detected to avert full-blown relapse (i.e. relapse detectable clinically and/or by conventional tests) and improve the probability of cure or long-term survival.

The difficulties in detecting MRD are complicated by the factors mentioned above, such as patchy distribution of and difficulty in accessing malignant cells.

Cancer treatment often suffers from a lack of long-term efficacy. Tumors can become resistant to therapy, at least in part by the accumulation of genetic aberrations that may not have been present during initial characterization and therapy. For example, in the case of multiple myeloma, there is often spatiotemporal heterogeneity in mutational status of focal lesions. Rasche L et al. Spatial genomic heterogeneity in multiple myeloma revealed by multi-region sequencing. Nat Commun 2017; 8: Article number 268, which is hereby incorporated by reference in its entirety.

However, current practice for diagnosis and prognosis involves sampling from a single site sequentially or different sites at different times, thereby missing an opportunity for complete profiling of the patient's cancer. Standard liquid biopsy and sequencing analysis of cell-free DNA from multiple myeloma patients, demonstrating similar heterogeneity in mutational profiles as concomitantly analyzed bone marrow samples, has demonstrated the utility of standard liquid biopsy in tumor profiling of cancers having high spatiotemporal heterogeneity in mutational profiles. Mithraprabhu S et al. Circulating tumour DNA analysis demonstrates spatial mutational heterogeneity that coincides with disease relapse in myeloma. Leukemia 2017; 31:1695-705, which is hereby incorporated by reference in its entirety.

Liquid biopsy techniques have been advanced over the past several years for the detection of circulating tumor cells (CTCs) and/or circulating tumor DNA (ctDNA) from liquid samples obtained from patients, e.g., blood samples. Liquid biopsies confer many advantages over traditional biopsy, being generally painless, non-invasive, and convenient. Indeed, CTCs detection years after surgical tumor resection have been correlated with poor clinical outcomes. Pantel K et al., Liquid biopsy and minimal residual disease—latest advances and implications for cure, Nat Rev Clin Oncol 2019; 16:409-24, which is hereby incorporated by reference in its entirety.

However, liquid biopsy techniques suffer from inadequate sensitivity, resulting in false negatives. For example, a ctDNA study using plasma samples from cancer patients exhibited sensitivity that varied from 59% in early lung cancer up to 86% in early head and neck cancers. The ctDNA study demonstrated sensitivity rates of 34% for stage I cancer, 77% for stage II, 84% for stage III, and 92% for stage IV across all tumor types (Liu et al 2019). Such results indicate that current liquid biopsy applications do not have the very high degree of sensitivity required for MRD detection in a significant proportion of patients. Such inadequate sensitivity likely stems from the low number of CTCs or ctDNA released into circulation during MRD states.

CXCR4 is expressed on hematopoietic stem cells (HSC) and plays a key role in their retention and maintenance in the bone marrow niche. The corresponding chemokine ligand for CXCR4 is CXCL12 (also known as SDF-1). The CXCR4/CXCL12 interaction plays an important role in the retention of HSC within the bone marrow. Fricker S P, Physiology and pharmacology of plerixafor, Transfus Med Hemother 2013; 40:237-45, which is hereby incorporated by reference in its entirety.

There exists a need for methods and systems for enhancing sensitivity of liquid biopsy techniques, in order to reduce false negatives in disease detection and prognosis. Such methods and systems would be particularly useful for, e.g., MRD detection, disease prognosis, and early disease detection. For example, such methods and systems would be useful for mass screening of otherwise normal individuals a realistic possibility with a high level of sensitivity that could enable identification of cancer when it's very early—and therefore, by definition, much more treatable/curable.

SUMMARY OF THE INVENTION

Provided herein is a method of analyzing a fluid sample obtained from a subject, comprising determining presence or absence of one or more tumor cells or tumor DNA in the fluid sample, wherein the subject was previously administered a cytokine or growth factor in an amount effective to mobilize release of the one or more tumor cells or tumor DNA into circulation.

Also provided herein is a method of detecting one or more tumor cells or tumor DNA in a fluid sample obtained from a subject, comprising: administering to the subject a cytokine or growth factor in an amount effective to stimulate release of the one or more tumor cells or tumor DNA into circulation; obtaining the fluid sample from the subject after administering the cytokine or growth factor to the subject;

and determining presence or absence of the released one or more tumor cells or tumor DNA in the fluid sample.

Also provided herein is a method of detecting presence or absence of minimal residual disease in a subject in need thereof, comprising: analyzing a fluid sample obtained from the subject or detecting one or more tumor cells or tumor DNA in a fluid sample obtained from the subject, according to a method disclosed herein, wherein (i) presence of the one or more tumor cells or tumor DNA in the fluid sample indicates presence of minimal residual disease in the subject, and (ii) absence of the one or more tumor cells or tumor DNA in the fluid sample indicates absence of minimal residual disease in the subject.

Also provided herein is a method of treating cancer in a subject in need thereof, comprising: administering to the subject a cytokine or growth factor in an amount effective to stimulate release of one or more tumor cells or tumor DNA into circulation; obtaining a fluid sample from the subject after administering the cytokine or growth factor to the subject; determining presence or absence of the released one or more tumor cells or tumor DNA in the fluid sample; and administering at least one cancer therapeutic to the subject if presence of the released one or more tumor cells or tumor DNA in the fluid sample is detected.

Also provided herein is a method of treating cancer in a subject in need thereof, comprising: administering at least one cancer therapeutic to the subject if one or more tumor cells or tumor DNA has been detected in a fluid sample obtained from the subject following administration of a cytokine or growth factor in an amount effective to stimulate release of the one or more tumor cells or tumor DNA into circulation of the subject.

In some embodiments, the cancer therapeutic is not an autologous HSC transplant.

Also provided herein is a method of prognosing a subject having cancer, comprising genetically profiling one or more tumor cells or tumor DNA analytes, wherein the one or more tumor cells or tumor DNA analytes were obtained from a fluid sample obtained from the subject, wherein the subject was previously administered a cytokine or growth factor in an amount effective to stimulate release of the one or more tumor cells or tumor DNA into circulation, wherein the genetic profile of the one or more tumor cells or tumor DNA analytes is indicative of the subject's prognosis.

Also provided herein is a method of prognosing a subject having cancer, comprising: administering to the subject a cytokine or growth factor in an amount effective to stimulate release of one or more tumor cells or tumor DNA analytes into circulation; obtaining a fluid sample from the subject after administering the cytokine or growth factor to the subject; and genetically profiling the released one or more tumor cells or tumor DNA analytes in the fluid sample, wherein the genetic profile of the one or more tumor cells or tumor DNA analytes is indicative of the subject's prognosis.

Also provided herein is a method of detecting cancer in a subject, comprising: detecting one or more tumor cells or tumor DNA analytes, wherein the one or more tumor cells or tumor DNA analytes were obtained from a fluid sample obtained from the subject, wherein the subject was previously administered a cytokine or growth factor in an amount effective to stimulate release of the one or more tumor cells or tumor DNA into circulation, wherein the detection of the one or more tumor cells or tumor DNA analytes is indicative of cancer in the subject.

Also provided herein is a method of detecting cancer in a subject, comprising: (a) administering to the subject a cytokine or growth factor in an amount effective to stimulate release of one or more tumor cells or tumor DNA analytes into circulation; (b) obtaining a fluid sample from the subject after administering the cytokine or growth factor to the subject; and (c) detecting the released one or more tumor cells or tumor DNA analytes in the fluid sample, wherein the detection of the one or more tumor cells or tumor DNA analytes is indicative of cancer in the subject.

In some embodiments, the cytokine or growth factor is selected from erythropoietin, G-CSF, GM-CSF, SCF, IL-3, KGF, and plerixafor. In an embodiment, the growth factor is plerixafor.

In some embodiments, the administering step further comprises administering to the subject one or more anticancer therapeutics.

In some embodiments, the anticancer therapeutic is selected from 5-Fluorouracil, 6-Mercaptopurine, 6-Thioguanine, Abemaciclib, Abiraterone Acetate, Acalabrutinib, Ado-Trastuzumab Emtansine, Afatinib Dimaleate, Aldesleukin, Alectinib, Alemtuzumab, Alpelisib, Amifostine, Aminolevulinic Acid Hydrochloride, Anastrozole, Apalutamide, Arsenic Trioxide, L-Asparaginase, Atezolizumab, Avelumab, Axitinib, Azacitidine, Belinostat, Bendamustine Hydrochloride, Bevacizumab, Bexarotene, Bicalutamide, Binimetinib, Bleomycin Sulfate, Blinatumomab, Bortezomib, Bosutinib, Brentuximab Vedotin, Brigatinib, Busulfan, Cabazitaxel, Cabozantinib-S-Malate, Calaspargase Pegol-mknl, Capecitabine, Caplacizumab-yhdp, Carboplatin, Carfilzomib, Carmustine, Carmustine Implant, Cemiplimab-rwlc, Ceritinib, Cetuximab, Chlorambucil, Cisplatin, Cladribine, Clofarabine, Cobimetinib, Copanlisib Hydrochloride, Corticosteroids, Crizotinib, Cyclophosphamide, Cytarabine, Dabrafenib Mesylate, Dacarbazine, Dacomitinib, Dactinomycin, Daratumumab, Darolutamide, Dasatinib, Daunorubicin Hydrochloride, Daunorubicin Hydrochloride and Cytarabine Liposome, Decitabine, Defibrotide Sodium, Degarelix, Denileukin Diftitox, Denosumab, Dexamethasone, Dexamethasone, Dexrazoxane Hydrochloride, Dinutuximab, Docetaxel, Doxorubicin Hydrochloride, Doxorubicin Hydrochloride Liposome, Durvalumab, Duvelisib, Elotuzumab, Eltrombopag Olamine, Emapalumab-lzsg, Enasidenib Mesylate, Encorafenib, Entrectinib, Enzalutamide, Epirubicin Hydrochloride, Erdafitinib, Eribulin Mesylate, Erlotinib Hydrochloride, Etoposide, Etoposide Phosphate, Everolimus, Exemestane, Fedratinib Hydrochloride, Fludarabine Phosphate, Flutamide, Fostamatinib Disodium, Fulvestrant, Gefitinib, Gemcitabine Hydrochloride, Gemtuzumab Ozogamicin, Gilteritinib Fumarate, Glasdegib Maleate, Glucarpidase, Goserelin Acetate, Hydroxyurea, Ibritumomab Tiuxetan, Ibrutinib, Idarubicin Hydrochloride, Idelalisib, Ifosfamide, Imatinib Mesylate, Imiquimod, Inotuzumab Ozogamicin, Interferon Alfa-2b, Recombinant, Iobenguane I 131, Ipilimumab, Irinotecan Hydrochloride, Irinotecan Hydrochloride Liposome, Ivosidenib, Ixabepilone, Ixazomib Citrate, Lanreotide Acetate, Lapatinib Ditosylate, Larotrectinib Sulfate, Lenalidomide, Lenvatinib Mesylate, Letrozole, Leuprolide Acetate, Lomustine, Lorlatinib, Mechlorethamine Hydrochloride, Megestrol Acetate, Melphalan, Methotrexate, Methylnaltrexone Bromide, Methylprednisolone, Midostaurin, Mitomycin C, Mitoxantrone Hydrochloride, Mogamulizumab-kpkc, Moxetumomab Pasudotox-tdfk, Necitumumab, Nelarabine, Neratinib Maleate, Netupitant and Palonosetron Hydrochloride, Nilotinib, Nilutamide, Niraparib Tosylate Monohydrate, Nivolumab, Obinutuzumab, Ofatumumab, Olaparib, Omacetaxine Mepesuccinate, Osimertinib Mesylate, Oxaliplatin, Paclitaxel, Paclitaxel Albumin-stabilized Nanoparticle Formulation, Palbociclib, Palifermin, Panitumumab, Panobinostat, Pazopanib Hydrochloride, Pegaspargase, Peginterferon Alfa-2b, Pembrolizumab, Pemetrexed Disodium, Pertuzumab, Polatuzumab Vedotin-piiq, Pomalidomide, Ponatinib Hydrochloride, Pralatrexate, Prednisone, Procarbazine Hydrochloride, Propranolol Hydrochloride, Raloxifene Hydrochloride, Ramucirumab, Ravulizumab-cwvz, Recombinant Interferon Alfa-2b, Regorafenib, Ribociclib, Rituximab, Rituximab and Hyaluronidase Human, Rolapitant Hydrochloride, Romidepsin, Romiplostim, Rucaparib Camsylate, Ruxolitinib Phosphate, Selinexor, Siltuximab, Sonidegib, Sorafenib Tosylate, Sunitinib Malate, Tagraxofusp-erzs, Talazoparib Tosylate, Tamoxifen Citrate, Temozolomide, Temsirolimus, Thalidomide, Thiotepa, Tocilizumab, Topotecan Hydrochloride, Toremifene, Trabectedin, Trametinib, Trastuzumab, Trastuzumab and Hyaluronidase-oysk, Trifluridine and Tipiracil Hydrochloride, Uridine Triacetate, Valrubicin, Vandetanib, Vemurafenib, Venetoclax, Vinblastine Sulfate, Vincristine Sulfate, Vincristine Sulfate Liposome, Vinorelbine Tartrate, Vismodegib, Vorinostat, Zanubrutinib, and Ziv-Aflibercept.

In some embodiments, the method comprises administering about 1 µg-1 g of the anticancer therapeutic to the subject.

In some embodiments, the fluid sample is a blood sample.

In some embodiments, the blood sample is a plasma or serum sample.

In some embodiments, the blood sample is a whole blood sample or a cellular fraction of a whole blood sample.

In some embodiments, the fluid sample is an ascites, cerebrospinal fluid, lymph, sweat, urine, tears, saliva, pleural fluid, pericardial fluid, cavity rinse, or organ rinse sample.

In some embodiments, the method comprises administering 0.1-0.4 mg/kg plerixafor or about 10-25 mg plerixafor to the subject.

In some embodiments, the method comprises administering about 0.24 mg/kg or about 20 mg plerixafor to the subject.

In some embodiments, the method comprises administering about 0.16 mg/kg or about 13 mg plerixafor to the subject.

In some embodiments, the method comprises administering plerixafor subcutaneously, intramuscularly, intravenously, or by inhalation.

In some embodiments, the method comprises administering plerixafor by subcutaneous injection.

In some embodiments, the plerixafor is administered daily for 1-4 days.

In some embodiments, the plerixafor is administered once prior to obtaining the fluid sample from the subject.

In some embodiments, the plerixafor is administered 6-48 hours prior to obtaining the fluid sample.

In some embodiments, the plerixafor is administered about 11 hours prior to obtaining the fluid sample.

In some embodiments, the cytokine or growth factor is administered after completing a round of treatment for cancer, optionally after completing sufficient number of rounds of chemotherapy to render the cancer undetectable by conventional means (i.e. achieve complete remission by conventional criteria excluding MRD detection).

In some embodiments, the cytokine or growth factor is administered when the subject is determined to be in remission or suspected by a clinician to be in complete remission from cancer.

In some embodiments, the subject is suspected to be in complete remission from cancer when the subject has completed a course of anticancer therapy.

In some embodiments, the determination of remission comprises detecting the presence or absence of plasma cells in a bone marrow sample of the subject.

In some embodiments, the detecting comprises performing a multiparametric flow cytometry assay on the bone marrow sample of the subject.

In some embodiments, the multiparametric flow cytometry comprises gating for any one or more of CD138, CD38, CD45, CD56, CD19, cytoplasmic κ and λ immunoglobulin light chains, CD20, CD27, CD28, CD81, CD117, CD200, CD54, CD229, CD319, and VS38c.

In some embodiments, the determination of remission comprises ASO-qPCR.

In some embodiments, the determination of remission comprises next generation sequencing.

In some embodiments, the administration of the cytokine or growth factor, the procurement of the fluid sample from the subject, and the determination of presence or absence of the released one or more tumor cells or tumor DNA is performed once.

In some embodiments, the administration of the cytokine or growth factor, the procurement of the fluid sample from the subject, and the determination of presence or absence of the released one or more tumor cells or tumor DNA is performed at least two times.

In some embodiments, the administration of the cytokine or growth factor, the procurement of the fluid sample from the subject, and the determination of presence or absence of the released one or more tumor cells or tumor DNA is performed after the subject has tested negative for minimal residual disease.

In some embodiments, the cancer is known to express CXCR4.

In some embodiments, the cancer is selected from adrenal cancer, anal cancer, bile duct cancer, bladder cancer, bone cancer, cancer of the brain or central nervous system, basal cell skin cancer, breast cancer, cervical cancer, colorectal cancer, endometrial cancer, esophageal cancer, eye cancer, gallbladder cancer, gastrointestinal carcinoid tumors, gastrointestinal stromal tumor (GIST), gastric cancer, glioma, glioblastoma, head and neck cancer (including head and neck squamous cell carcinoma), Hodgkin's disease, diffuse large B cell lymphoma, follicular lymphoma, Kaposi sarcoma, kidney cancer, laryngeal and hypopharyngeal cancer, leukemia (including acute and chronic leukemia involving the lymphoid, myeloid, both or unclassified lineages), liver cancer (including hepatocellular carcinoma), lymphoma, melanoma (including unresectable or metastatic melanoma), prostate cancer, lung cancer (including non-small cell lung cancer and metastatic non-small cell lung cancer), malignant mesothelioma, merkel cell carcinoma, metastatic urothelial carcinoma, multiple myeloma, myelodysplastic syndrome, nasal cavity and paranasal sinus cancer, nasopharyngeal cancer, neuroendocrine cancer, neuroblastoma, non-Hodgkin lymphoma, oral cavity and oropharyngeal cancer, osteosarcoma, ovarian cancer, pancreatic cancer, penile cancer, pituitary tumors, renal cancer (including renal cell carcinoma), retinoblastoma, hematological malignancy, rhabdomyosarcoma, salivary gland cancer, sarcoma, squamous cell skin cancer, small intestine cancer, stomach cancer, testicular cancer, thymus cancer, thyroid cancer, uterine cancer, and vaginal cancer.

In some embodiments, the cancer is selected from hematological malignancy, breast cancer, colorectal cancer, esophageal cancer, head and neck cancer, renal cancer, lung cancer, gynecologic cancer, liver cancer, prostate cancer and gallbladder cancer.

In some embodiments, the cancer is multiple myeloma.

In some embodiments, the one or more tumor cells or tumor DNA is released into circulation from a non-blood compartment.

In some embodiments, the non-blood compartment is a bone marrow compartment.

In some embodiments, the presence or absence of the released one or more tumor cells or tumor DNA in the fluid sample is determined by flow cytometry.

In some embodiments, the flow cytometry comprises multiparameter flow cytometry.

In some embodiments, the multiparametric flow cytometry comprises gating for any one or more of CD138, CD38, CD45, CD56, CD19, cytoplasmic κ and λ immunoglobulin light chains, CD20, CD27, CD28, CD81, CD117, CD200, CD54, CD229, CD319, and VS38c.

In some embodiments, the presence or absence of the released one or more tumor cells or tumor DNA in the fluid sample is determined by sequence analysis.

In some embodiments, the sequence analysis comprises PCR, optionally Aso-qPCR.

In some embodiments, the sequence analysis comprises sequencing.

In some embodiments, the sequencing comprises deep sequencing.

In some embodiments, the sequencing comprises deep sequencing of the VDJ region.

In some embodiments, the presence or absence of the released one or more tumor cells or tumor DNA in the fluid sample is determined by an assay with a sensitivity of at least 1 in 100,000 cells.

In some embodiments, the method further comprises terminating cancer treatment if the fluid sample shows absence of tumor cells and tumor DNA.

Also provided herein is a kit, comprising a pharmaceutically acceptable dosage form of a growth factor or cytokine and instructions for use according to a method described herein.

Also provided herein is a system for liquid biopsy yield enhancement, comprising one or more pharmaceutically acceptable dosage forms of a cytokine or growth factor; one or more reagents, devices, or kits for obtaining a fluid sample from a subject in need thereof; and one or more reagents, devices, and/or apparatuses for analyzing tumor cells and/or tumor DNA in the fluid sample.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 depicts the structure of plerixafor.

DETAILED DESCRIPTION OF THE INVENTION

Definitions

Terms used in the claims and specification are defined as set forth below unless otherwise specified.

The term "subject" as used herein includes both humans and non-humans and include but is not limited to humans, non-human primates, canines, felines, murines, bovines, equines, and porcines. In particular embodiments, the subject is a human subject.

The terms "polynucleotides," "nucleic acid," and "nucleotides" are used interchangeably to refer to a polymeric form of nucleotides of any length, either deoxyribonucleotides or ribonucleotides, or analogs thereof. The nucleic acids can be RNA, DNA, e.g., genomic DNA, mitochondrial DNA, viral DNA, synthetic DNA, or cDNA reverse transcribed from RNA.

The term "diseased polynucleotides" as used herein refer to polynucleotides from a diseased cell, e.g., a tumor or cancer cell, or polynucleotides comprising a genetic profile, e.g., one or more genetic abnormalities associated with the disease.

The terms "co-administration" or "co-administer," as used herein, refer to the administration of two or more agents, such that the two or more agents are administered as part of the same course of therapy. In some embodiments, two or more agents are co-administered when such agents are administered simultaneously. In some embodiments, two or more agents are "co-administered" when such agents are administered separately, as long as the effects of the agents co-occur in the subject's body. In some embodiments, two or more agents are "co-administered" when such agents are administered separately, as long as one or more of the administered agents act to enhance or modulate the effect of the other administered agent(s).

The term "sufficient amount" means an amount sufficient to produce a desired effect, e.g., an amount sufficient to mobilize diseased cells or diseased polynucleotides into circulation.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Overview

Provided herein are methods, kits, and systems for liquid biopsy that enhance the yield of diseased cells, diseased circulating nucleic acids, or combinations thereof in a liquid biological sample obtained from a subject. Such methods, kits, and systems utilize one or more mobilizing agents that mobilize diseased cells or their debris from their niches into circulation of the subject, thereby enhancing yield of the liquid biopsy. The mobilized release of the one or more diseased cells or disease-associated polynucleotides into circulation, and subsequent collection of a fluid sample comprising such material, is referred to herein as liquid biopsy yield enhancement (LBYE).

"Release" of diseased cells or their debris "into circulation" is used herein to refer to release of the cells or debris (e.g., diseased polynucleotides) into a fluid compartment of the subject, such that the diseased cells or debris can be obtained and/or detected in a fluid sample obtained from the subject. In some embodiments, the release of the diseased cells or their debris into circulation comprises release into the bloodstream of the subject, such that they can be obtained and/or collected in a blood sample obtained from the subject. In some embodiments, the release of the diseased cells or their debris into circulation comprises release into an extracellular fluid compartment, such that they can be obtained and/or collected in another type of fluid sample obtained from the subject. Exemplary fluid samples are disclosed herein. It is to be understood that the diseased cells and/or diseased polynucleotides can be released into circulation from any organ or tissue of the body. In some embodiments, the diseased cells and/or diseased polynucleotides are released into circulation from the subject's tumor. In some embodiments, the diseased cells and/or diseased polynucleotides are released into circulation from the subject's bone marrow.

In some embodiments, the one or more mobilizing agents comprises a cytokine or growth factor.

Accordingly, provided herein is a method of analyzing a fluid sample obtained from a subject, comprising determining presence or absence of one or more disease cells or disease-associated polynucleotides in the fluid sample, wherein the subject was previously administered a mobilizing agent in an amount effective to mobilize release of the one or more disease cells or disease-associated polynucleotides into circulation.

Also provided herein is a method of detecting one or more diseased cells or disease-associated polynucleotides in a fluid sample obtained from a subject, comprising: (a) administering to the subject a cytokine or growth factor in an amount effective to stimulate release of the one or more tumor cells or tumor DNA into circulation; (b) obtaining the fluid sample from the subject after administering the cytokine or growth factor to the subject; and (c) determining presence or absence of the released one or more tumor cells or tumor DNA in the fluid sample.

Exemplary Mobilizing Agents

In some embodiments, the one or more mobilizing agents comprises a cytokine or growth factor.

In some embodiments, the cytokine or growth factor is a CXCR4 antagonist. Exemplary CXCR4 antagonists include, but are not limited to, plerixafor, TG-0054, AMD070, FC122, FC131. Exemplary CXCR4 antagonists are described in Debnath et al., Small molecule inhibitors of CXCR4, Theranostics. 2013; 3(1):47-75, which is hereby incorporated by reference in its entirety.

In a preferred embodiment, the CXCR4 antagonist is plerixafor. The IUPAC name for plerixafor is 1-{[4-(1,4,8,11-tetrazacyclotetradec-1-ylmethyl)phenyl]methyl}-1,4,8,11-tetrazacyclotetradecane). The chemical structure of plerixafor is shown in FIG. 1. Plerixafor is an FDA approved treatment, used to mobilize HSC into circulation for collection and autologous transplant for the treatment of multiple myeloma and non-Hodgkin's lymphoma. Plerixafor has been shown to rapidly mobilize HSC within hours.

In some embodiments, the plerixafor is administered to the subject subcutaneously. In some embodiments, the plerixafor is administered to the subject intramuscularly. In some embodiments, the plerixafor is administered to the subject intravenously. In some embodiments, the plerixafor is administered to the subject by inhalation. In preferred embodiments, the plerixafor is administered to the subject subcutaneously.

In some embodiments, the plerixafor is administered to the subject once daily. In some embodiments, the plerixafor is administered to the subject once daily for 1-10 days, 1-8 days, 1-6 days, or preferably 1-4 days. In some embodiments, the plerixafor is administered once daily for one day. In some embodiments, the plerixafor is administered once daily for two days, three days, or four days.

In some embodiments, 0.1-0.4 mg/kg plerixafor is administered to the subject. In some embodiments, 0.24 mg/kg plerixafor is administered to the subject. In some embodiments, 0.16 mg/kg plerixafor is administered to the subject. For example, if the subject has an estimated creatinine clearance of less than 50 ml/min, the subject may be administered 0.16 mg/kg of the plerixafor. Preferably, the plerixafor is administered subcutaneously.

In some embodiments, 20 mg plerixafor is administered to the subject. In some embodiments, 13 mg plerixafor is administered to the subject. For example, if the subject has an estimated creatinine clearance of less than 50 ml/min, the subject may be administered 13 mg plerixafor.

In some embodiments, the plerixafor is administered 48 hours or less prior to collection of the fluid sample from the subject. In some embodiments, the plerixafor is administered 36 hours or less prior to collection of the fluid sample from the subject. In some embodiments, the plerixafor is administered 24 hours or less prior to collection of the fluid sample from the subject. In some embodiments, the plerixafor is administered 20 hours or less prior to collection of the fluid sample from the subject. In some embodiments, the plerixafor is administered 16 hours or less prior to collection of the fluid sample from the subject. In some embodiments, the plerixafor is administered 12 hours or less prior to collection of the fluid sample from the subject. In some embodiments, the plerixafor is administered about 11 hours prior to collection of the fluid sample from the subject. In some embodiments, the plerixafor is administered about 6-48 hours prior to collection of the fluid sample from the subject. In some embodiments, the plerixafor is administered about 8-24 hours prior to collection of the fluid sample from the subject. In some embodiments, the plerixafor is administered about 10-14 hours prior to collection of the fluid sample from the subject.

In some embodiments, the cytokine or growth factor is G-CSF. In some embodiments, 1-30 µg/kg G-CSF is administered to the subject. In some embodiments, 5-20 µg/kg G-CSF is administered to the subject. In some embodiments, about 10 micrograms/kg of G-CSF is administered to the subject. In some embodiments, about 300 µg is administered to a subject weighing 70 kg or less. In some embodiments, about 480 µg is administered to a subject weighing over 70 kg.

In some embodiments, G-CSF is administered to the subject once daily. In some embodiments, G-CSF is administered to the subject once daily for 1-10 days, 1-8 days, 1-6 days, or preferably 1-4 days. In some embodiments, G-CSF is administered once daily for one day. In some embodiments, G-CSF is administered once daily for two days, three days, or four days.

In particular embodiments, G-CSF and plerixafor are co-administered to the subject. In some embodiments, G-CSF is administered to the subject prior to administration of plerixafor, such that G-CSF administration primes or enhances the mobilizing effects of the plerixafor on the diseased cells or polynucleotides. In some embodiments, G-CSF is co-administered to the subject at the same time as the plerixafor or following plerixafor administration.

In some embodiments of G-CSF and plerixafor co-administration, the G-CSF and plerixafor are co-administered to the subject once daily for one day. In another exemplary embodiment, the G-CSF and plerixafor are co-administered to the subject once daily for two days. In particular embodiments, about 5-20 µg/kg of G-CSF and about 0.1-0.4 mg/kg of plerixafor are co-administered to the subject. In particular embodiments, about and about 10 micrograms/kg of G-CSF and about 0.24 mg/kg plerixafor are co-administered to the subject. In particular embodiments, about 10 micrograms/kg of G-CSF and about 0.16 mg/kg plerixafor are co-administered to the subject.

In an exemplary embodiment of G-CSF and plerixafor administration, G-CSF is administered to the subject once daily for 1-4 days at the dose of 5-20 µg/kg, optionally rounded off to the nearest vial size. In particular embodiments, 10 micrograms/kg of G-CSF is administered to the subject once daily for 1-4 days. Once the subject has received G-CSF once daily for 1-4 days, plerixafor administration is initiated. The plerixafor is administered once daily for 1-4 days. The subject's fluid sample is collected within 48 hours of the last plerixafor administration, e.g., around 11 hours after the last plerixafor administration.

In an exemplary embodiment of G-CSF and plerixafor co-administration, G-CSF is administered to the subject once daily for one day, followed by commencement of plerixafor administration the following day. In an exemplary embodiment of G-CSF and plerixafor co-administration, G-CSF is administered to the subject once daily for two days, followed by commencement of plerixafor administration the following day. In an exemplary embodiment of G-CSF and plerixafor co-administration, G-CSF is administered to the subject once daily for three days, followed by commencement of plerixafor administration the following day. In an exemplary embodiment of G-CSF and plerixafor co-administration, G-CSF is administered to the subject once daily for four days, followed by commencement of plerixafor administration the following day.

In some embodiments, the cytokine or growth factor is GM-CSF. In some embodiments, 1-30 µg/kg GM-CSF is administered to the subject. In some embodiments, 5-20 µg/kg GM-CSF is administered to the subject. In some embodiments, about 10 micrograms/kg of GM-CSF is administered to the subject. In some embodiments, about 300 µg is administered to a subject weighing 70 kg or less. In some embodiments, about 480 µg is administered to a subject weighing over 70 kg.

In some embodiments, GM-CSF is administered to the subject once daily. In some embodiments, GM-CSF is administered to the subject once daily for 1-10 days, 1-8 days, 1-6 days, or preferably 1-4 days. In some embodiments, GM-CSF is administered once daily for one day. In some embodiments, GM-CSF is administered once daily for two days, three days, or four days.

In particular embodiments, GM-CSF and plerixafor are co-administered to the subject. In some embodiments, GM-CSF is administered to the subject prior to administration of plerixafor, such that GM-CSF administration primes or enhances the mobilizing effects of the plerixafor on the diseased cells or polynucleotides. In some embodiments, GM-CSF is co-administered to the subject at the same time as the plerixafor or following plerixafor administration.

In some embodiments of GM-CSF and plerixafor co-administration, the GM-CSF and plerixafor are co-administered to the subject once daily for one day. In another exemplary embodiment, the GM-CSF and plerixafor are co-administered to the subject once daily for two days. In particular embodiments, about 5-20 µg/kg of GM-CSF and about 0.1-0.4 mg/kg of plerixafor are co-administered to the subject. In particular embodiments, about and about 10 micrograms/kg of GM-CSF and about 0.24 mg/kg plerixafor are co-administered to the subject. In particular embodiments, about 10 micrograms/kg of GM-CSF and about 0.16 mg/kg plerixafor are co-administered to the subject.

In an exemplary embodiment of GM-CSF and plerixafor administration, GM-CSF is administered to the subject once daily for 1-4 days at the dose of 5-20 µg/kg, optionally rounded off to the nearest vial size. In particular embodiments, 10 micrograms/kg of GM-CSF is administered to the subject once daily for 1-4 days. Once the subject has received GM-CSF once daily for 1-4 days, plerixafor administration is initiated. The plerixafor is administered once daily for 1-4 days. The subject's fluid sample is collected within 48 hours of the last plerixafor administration, e.g., around 11 hours after the last plerixafor administration.

In an exemplary embodiment of GM-CSF and plerixafor co-administration, GM-CSF is administered to the subject once daily for one day, followed by commencement of plerixafor administration the following day. In an exemplary embodiment of GM-CSF and plerixafor co-administration, GM-CSF is administered to the subject once daily for two days, followed by commencement of plerixafor administration the following day. In an exemplary embodiment of GM-CSF and plerixafor co-administration, GM-CSF is administered to the subject once daily for three days, followed by commencement of plerixafor administration the following day. In an exemplary embodiment of GM-CSF and plerixafor co-administration, GM-CSF is administered to the subject once daily for four days, followed by commencement of plerixafor administration the following day.

In some embodiments, the cytokine or growth factor is SCF. In some embodiments, the SCF is r-metHuSCF, described in Lapierre V et al., Ancestim (r-metHuSCF) plus filgrastim and/or chemotherapy for mobilization of blood progenitors in 513 poorly mobilizing cancer patients: the French compassionate experience, Bone Marrow Transplantation (2011) 46:936-942, which is hereby incorporated by reference in its entirety. In some embodiments, about 20 µg/kg r-metHuSCF is administered to the subject daily for 1-21 days. In some embodiments, about 20 µg/kg r-metHuSCF is administered to the subject daily for 1-10 days. In some embodiments, about 20 µg/kg r-metHuSCF is administered to the subject daily for 1-4 days, 1-3 days, 1-2 days, or for one day. In some embodiments, prior to the SCF treatment, the subject is pretreated with an anti-allergy medication, e.g., ranitidine. In some embodiments, about 20 µg/kg r-metHuSCF is co-administered to the subject with filgrastim. In some embodiments of co-administration of r-metHuSCF with filgrastim, about 1-20 µg/kg filgrastim is administered to the subject. In some embodiments of co-administration of r-metHuSCF with filgrastim, about 5-10 µg/kg filgrastim is administered to the subject.

In some embodiments, the cytokine or growth factor is IL-3. In some embodiments, about 5-10 µg/kg of IL-3 is administered to the subject.

In some embodiments, the cytokine or growth factor is erythropoietin. In some embodiments, about 10,000-40,000 U of erythropoietin is administered to the subject. In some embodiments, the erythropoietin is Aranesp®. In some embodiments, about 100-400 µg of Aranesp® is administered to the subject.

In some embodiments, the cytokine or growth factor is KGF (keratinocyte growth factor, palifermin). In some embodiments, palifermin is administered at the dose of 10-100 mcg/kg per day for 1-3 days.

In some embodiments wherein the disease is cancer, the mobilizing agent is co-administered with an anticancer therapeutic. Any anticancer therapeutic known in the art may be co-administered with the mobilizing agent. In some embodiments, the anticancer therapeutic is a chemotherapeutic. In some embodiments, a combination of more than one anticancer therapeutic is used. Many chemotherapeutics are known in the art. Exemplary anti-cancer agents include, but are not limited to 5-Fluorouracil, 6-Mercaptopurine, 6-Thioguanine, Abemaciclib, Abiraterone Acetate, Acalabrutinib, Ado-Trastuzumab Emtansine, Afatinib Dimaleate, Aldesleukin, Alectinib, Alemtuzumab, Alpelisib, Amifostine, Aminolevulinic Acid Hydrochloride, Anastrozole, Apalutamide, Arsenic Trioxide, L-Asparaginase, Atezolizumab, Avelumab, Axitinib, Azacitidine, Belinostat, Bendamustine Hydrochloride, Bevacizumab, Bexarotene, Bicalutamide, Binimetinib, Bleomycin Sulfate, Blinatumomab, Bortezomib, Bosutinib, Brentuximab Vedotin, Brigatinib, Busulfan, Cabazitaxel, Cabozantinib-S-Malate, Calaspargase Pegol-mknl, Capecitabine, Caplacizumab-yhdp, Carboplatin, Carfilzomib, Carmustine, Carmustine Implant, Cemiplimab-rwlc, Ceritinib, Cetuximab, Chlorambucil, Cisplatin, Cladribine, Clofarabine, Cobimetinib, Copanlisib Hydrochloride, Corticosteroids, Crizotinib, Cyclophosphamide, Cytarabine, Dabrafenib Mesylate, Dacarbazine, Dacomitinib, Dactinomycin, Daratumumab, Darolutamide, Dasatinib, Daunorubicin Hydrochloride, Daunorubicin Hydrochloride and Cytarabine Liposome, Decitabine, Defibrotide Sodium, Degarelix, Denileukin Diftitox, Denosumab, Dexamethasone, Dexamethasone, Dexrazoxane Hydrochloride, Dinutuximab, Docetaxel, Doxorubicin Hydrochloride, Doxorubicin Hydrochloride Liposome, Durvalumab, Duvelisib, Elotuzumab, Eltrombopag Olamine, Emapalumab-lzsg, Enasidenib Mesylate, Encorafenib, Entrectinib, Enzalutamide, Epirubicin Hydrochloride, Erdafitinib, Eribulin Mesylate, Erlotinib Hydrochloride, Etoposide, Etoposide Phosphate, Everolimus, Exemestane, Fedratinib Hydrochloride, Fludarabine Phosphate, Flutamide, Fostamatinib Disodium, Fulvestrant, Gefitinib, Gemcitabine Hydrochloride, Gemtuzumab Ozogamicin, Gilteritinib Fumarate, Glasdegib Maleate, Glucarpidase, Goserelin Acetate, Hydroxyurea, Ibritumomab Tiuxetan, Ibrutinib, Idarubicin Hydrochloride, Idelalisib, Ifosfamide, Imatinib Mesylate, Imiquimod, Inotuzumab Ozogamicin, Interferon Alfa-2b, Recombinant, Iobenguane I 131, Ipilimumab, Irinotecan Hydrochloride, Irinotecan Hydrochloride Liposome, Ivosidenib, Ixabepilone, Ixazomib Citrate, Lanreotide Acetate, Lapatinib Ditosylate, Larotrectinib Sulfate, Lenalidomide, Lenvatinib Mesylate, Letrozole, Leuprolide Acetate, Lomustine, Lorlatinib, Mechlorethamine Hydrochloride, Megestrol Acetate, Melphalan, Methotrexate, Methylnaltrexone Bromide, Methylprednisolone, Midostaurin, Mitomycin C, Mitoxantrone Hydrochloride, Mogamulizumab-kpkc, Moxetumomab Pasudotox-tdfk, Necitumumab, Nelarabine, Neratinib Maleate, Netupitant and Palonosetron Hydrochloride, Nilotinib, Nilutamide, Niraparib Tosylate Monohydrate, Nivolumab, Obinutuzumab, Ofatumumab, Olaparib, Omacetaxine Mepesuccinate, Osimertinib Mesylate, Oxaliplatin, Paclitaxel, Paclitaxel Albumin-stabilized Nanoparticle Formulation, Palbociclib, Palifermin, Panitumumab, Panobinostat, Pazopanib Hydrochloride, Pegaspargase, Peginterferon Alfa-2b, Pembrolizumab, Pemetrexed Disodium, Pertuzumab, Polatuzumab Vedotin-piiq, Pomalidomide, Ponatinib Hydrochloride, Pralatrexate, Prednisone, Procarbazine Hydrochloride, Propranolol Hydrochloride, Raloxifene Hydrochloride, Ramucirumab, Ravulizumab-cwvz, Recombinant Interferon Alfa-2b, Regorafenib, Ribociclib, Rituximab, Rituximab and Hyaluronidase Human, Rolapitant Hydrochloride, Romidepsin, Romiplostim, Rucaparib Camsylate, Ruxolitinib Phosphate, Selinexor, Siltuximab, Sonidegib, Sorafenib Tosylate, Sunitinib Malate, Tagraxofusp-erzs, Talazoparib Tosylate, Tamoxifen Citrate, Temozolomide, Temsirolimus, Thalidomide, Thiotepa, Tocilizumab, Topotecan Hydrochloride, Toremifene, Trabectedin, Trametinib, Trastuzumab, Trastuzumab and Hyaluronidase-oysk, Trifluridine and Tipiracil Hydrochloride, Uridine Triacetate, Valrubicin, Vandetanib, Vemurafenib, Venetoclax, Vinblastine Sulfate, Vincristine Sulfate, Vincristine Sulfate Liposome, Vinorelbine Tartrate, Vismodegib, Vorinostat, Zanubrutinib, and Ziv-Aflibercept.

In some embodiments, the anticancer therapeutic is a therapeutic antibody, e.g., monoclonal antibody, or antigen-binding fragment thereof. The therapeutic antibody may be selective for an anti-tumor antigen, e.g., an antigen associated with the subject's cancer type or an antigen associated with the subject's tumor.

In particular embodiments, wherein the subject is suspected to harbor residual disease but is in complete remission by conventional criteria, the cytokine or growth factor is co-administered with an appropriate dose of an anticancer therapeutic. The anticancer therapeutic may kill or inactivate any cancer cells that have been released into circulation, to prevent their engraftment at other sites. A physician may determine the appropriate anticancer therapeutic for inactivating the released cancer cells, while minimizing unnecessary side effects. A physician may determine the dosage regimen of the co-administered anticancer therapeutic which he or she considers appropriate for inactivating the released cancer cells, while minimizing unnecessary side effects. The physician may consider several factors in the determination, such as, e.g., the subject's medical history, the type of disease (e.g., type of cancer), the subject's age, body weight, gender, past response to therapeutic intervention, and the like. In some embodiments, about 1 µg-1 g of the anticancer therapeutic is co-administered with the plerixafor.

Exemplary Diseases

In some embodiments, the disease is cancer. One or more LBYE methods described herein are useful for prognosis or minimal residual disease detection for any type of cancer. Exemplary cancers include adrenal cancer, anal cancer, bile duct cancer, bladder cancer, bone cancer, cancer of the brain or central nervous system, basal cell skin cancer, breast cancer, cervical cancer, colorectal cancer, endometrial cancer, esophageal cancer, eye cancer, gallbladder cancer, gastrointestinal carcinoid tumors, gastrointestinal stromal tumor (GIST), gastric cancer, glioma, glioblastoma, head and neck cancer (including head and neck squamous cell carcinoma), Hodgkin's disease, diffuse large B cell lymphoma, follicular lymphoma, Kaposi sarcoma, kidney cancer, laryngeal and hypopharyngeal cancer, leukemia (including acute and chronic leukemia involving the lymphoid, myeloid, both or unclassified lineages), liver cancer (including hepatocellular carcinoma), lymphoma, melanoma (including unresectable or metastatic melanoma), prostate cancer, lung cancer (including non-small cell lung cancer and metastatic non-small cell lung cancer), malignant mesothelioma, merkel cell carcinoma, metastatic urothelial carcinoma, multiple myeloma, myelodysplastic syndrome, nasal cavity and paranasal sinus cancer, nasopharyngeal cancer, neuroendocrine cancer, neuroblastoma, non-Hodgkin lymphoma, oral cavity and oropharyngeal cancer, osteosarcoma, ovarian cancer, pancreatic cancer, penile cancer, pituitary tumors, renal cancer (including renal cell carcinoma), retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, or vaginal cancer.

In some embodiments, the cancer is associated with CXCR4 expression. Exemplary cancers associated with CXCR4 expression are described in Zhao, Hongli et al. "CXCR4 over-expression and survival in cancer: a system review and meta-analysis." *Oncotarget* vol. 6, 7 (2015): 5022-40, which is hereby incorporated by reference in its entirety. Such cancers include, but are not limited to hematological malignancy, breast cancer, colorectal cancer, esophageal cancer, head and neck cancer, renal cancer, lung cancer, gynecologic cancer, liver cancer, prostate cancer and gallbladder cancer. Hematological malignancies include, e.g., multiple myeloma, Hodgkin's disease, non-Hodgkin lymphoma, acute leukemia, chronic leukemia, and myelodysplastic syndrome.

In particular embodiments, the cancer is multiple myeloma.

Exemplary Fluid Samples and Fluid Sample Processing

In some embodiments, the fluid sample is a whole blood sample. In some embodiments, the fluid sample is a plasma or serum sample. In some embodiments, the fluid sample is an ascites, cerebrospinal fluid, sweat, urine, tears, saliva, pleural fluid, pericardial fluid, lymph, cavity rinse, or organ rinse sample. The liquid sample can be an essentially cell-free liquid sample (e.g., plasma, serum, sweat, urine, tears, etc.). In some embodiments, the liquid sample is not essentially cell-free.

In some embodiments, a whole blood sample is obtained from the subject. The whole blood sample may be separated into fractions, e.g., cellular and non-cellular fractions. The cellular fraction may be assessed for the presence or absence of one or more CTCs. The non-cellular fraction (e.g., plasma or serum) may be assessed for the presence or absence of ctDNA.

In an exemplary embodiment, a whole blood sample is separated into fractions using a Ficoll reagent (e.g., Ficoll-Paque PLUS, GE Healthcare). In some embodiments, a blood sample combined with Ficoll is subjected to density based centrifugation, resulting in splitting of the components into four distinct layers: (1) a red blood cell layer, (2) a Ficoll layer, (3) a mononuclear layer which contains white blood cells and other nucleated cells (e.g. CTCs) and (4) a plasma layer.

In some embodiments, one or more enrichment steps is performed on a cellular fraction of a blood sample, or a whole blood sample to enrich for CTCs. A skilled artisan may utilize any CTC enrichment process known in the art, including but not limited to those that enrich for CTCs by separating CTCs from other cells found in the blood. CTCs may be separated from other cells by physical properties, such as, e.g., size, density, electrical charge, and deformability. CTCs may be separated from other cells by biological properties, e.g., by positive or negative selection based on biomarker profile. Biomarker detection reagents, e.g., antibodies, may be selected based on the subject's tumor type and tumor profile. Exemplary methods for CTC enrichment are described in Harouaka, Ramdane A et al. "Circulating tumor cell enrichment based on physical properties." *Journal of laboratory automation* vol. 18, 6 (2013): 455-68. doi:10.1177/2211068213494391, which is hereby incorporated by reference in its entirety.

An exemplary system for CTC enrichment includes the EasySep™ Direct Human CTC Enrichment (StemCell Technologies), and CellSearch® (Veridex, LLC, Raritan, N.J., USA).

Detection/Analysis of Diseased Cells or Disease-Associated Polynucleotides

The presence of absence of diseased cells in the fluid sample may be determined by any means known in the art.

In some embodiments, the diseased cells in the fluid sample are circulating tumor cells (CTCs). The CTCs may be from any one of the cancers disclosed herein. In some embodiments, the CTCs are from a cancer associated with CXCR4 expression. In some embodiments, the CTCs are from a hematological malignancy. In particular embodiments, the CTCs are from multiple myeloma. Exemplary cancers, cancers associated with CXCR4 expression, and hematological malignancies are disclosed herein.

In particular embodiments, the CTCs are detected using one or more biomarkers specific for the tumor.

In particular embodiments wherein the cancer is multiple myeloma, the one or more biomarkers are selected from CD138, CD38, CD45, CD56, CD19, cytoplasmic κ and λ immunoglobulin light chains, CD20, CD27, CD28, CD81, CD117, CD200, CD54, CD229, CD319, and VS38c. In particular embodiments wherein the cancer is multiple myeloma, the one or more biomarkers are selected from CD138, CD38, CD45, CD56, CD19, and cytoplasmic κ and λ immunoglobulin light chains. In particular embodiments wherein the cancer is multiple myeloma, the one or more biomarkers are selected from CD19, CD45, CD56, CD81, CD27, CD117, and cytoplasmic κ and λ immunoglobulin light chains. The one or more biomarkers may be positive or negative markers. In some embodiments, wherein the cancer is multiple myeloma, the CTCs are detected using multiparametric flow cytometry for the one or more biomarkers. In some embodiments, the multiparametric flow cytometry comprises gating for any one or more of CD138, CD38, CD45, CD56, CD19, cytoplasmic κ and λ immunoglobulin light chains, CD20, CD27, CD28, CD81, CD117, CD200, CD54, CD229, CD319, and VS38c. In particular embodiments, the multiparametric flow cytometry comprises gating for any one or more of CD138, CD38, CD45, CD56, CD19, and cytoplasmic κ and λ immunoglobulin light chains. In other particular embodiments, the multiparametric flow cytometry comprises gating for CD19, CD45, CD56, CD81, CD27, CD117, and cytoplasmic κ and λ immunoglobulin light chains. In preferred embodiments, the multiparametric flow cytometry comprises gating for CD138. In some embodiments, wherein the subject had been previously treated with an anticancer therapy comprising a monoclonal antibody against CD38 or CD138, the multiparametric flow cytometry comprises gating for any one or more of CD54, CD229, CD319, and VS38c. Multiparametric flow cytometry methods for detection of multiple myeloma are described herein, and in the following references: Kumar S et al. International Myeloma Working Group consensus criteria for response and minimal residual disease assessment in multiple myeloma. Lancet Oncol 2016; 17:e328-46; WO2017198879A1; Flores-Montero J, Sanoja-Flores L, Paiva B, et al. Next generation flow for highly sensitive and standardized detection of minimal residual disease in multiple myeloma. Leukemia 2017; 31:2094-2103; Mishima Y et al., The Mutational Landscape of Circulating Tumor Cells in Multiple Myeloma, Cell Rep. 2017 Apr. 4; 19(1): 218-224. doi:10.1016/j.celrep.2017.03.025; US20180140664A1, each of which is hereby incorporated by reference in its entirety.

In particular embodiments wherein the cancer is multiple myeloma, ASO-qPCR to may be used to detect presence or absence of multiple myeloma CTCs in the fluid sample. Exemplary ASO-qPCR techniques are described in Kumar S et al. International Myeloma Working Group consensus criteria for response and minimal residual disease assessment in multiple myeloma. Lancet Oncol 2016; 17:e328-46, which is hereby incorporated by reference in its entirety.

In some embodiments, the CTCs from the fluid sample are analyzed by sequencing, e.g., single cell sequencing. The sequencing can comprise whole exome sequencing, whole genome sequencing, targeted sequencing of a panel of cancer genes, or targeted sequencing of a single cancer gene. The sequencing can comprise next generation sequencing, e.g., as described herein. The sequencing can comprise deep sequencing, e.g., deep sequencing of the VDJ region.

In particular embodiments wherein the cancer is lymphoma, the one or more biomarkers are selected from CD4, CD5, CD8, CD10, CD19, CD20, CD22, CD23, CD30, CD38, and surface κ and λ immunoglobulin light chains.

In some embodiments, the biomarker is detected by antibody staining. In particular embodiments, cells that are positive for the biomarker are detected by flow cytometry.

The presence or absence of diseased circulating nucleic acids in the fluid sample may be determined by any means known in the art.

In some embodiments, cell-free or circulating nucleic acids may be isolated from the fluid sample, e.g., a cell-free fluid sample. Nucleic acid can be isolated from the sample using any means known in the art. For example, nucleic acid can be extracted from the sample using liquid extraction (e.g., Trizol, DNAzol) techniques. Nucleic acid can also be extracted using commercially available kits (e.g., Qiagen DNeasy kit, QIAamp kit, Qiagen Midi kit, QIAprep spin kit).

Nucleic acid can be concentrated by known methods, including, by way of example only, centrifugation. Nucleic acid can be bound to a selective membrane (e.g., silica) for the purposes of purification. Nucleic acid can also be enriched for fragments of a desired length, e.g., fragments which are less than 1000, 500, 400, 300, 200 or 100 base pairs in length. Such an enrichment based on size can be performed using, e.g., PEG-induced precipitation, an electrophoretic gel or chromatography material (Huber et al. (1993) Nucleic Acids Res. 21:1061-6), gel filtration chromatography, TSK gel (Kato et al. (1984) J. Biochem, 95:83-86), which publications are hereby incorporated by reference.

Polynucleotides extracted from a biological sample can be selectively precipitated or concentrated using any methods known in the art.

The nucleic acid sample can be enriched for target polynucleotides. Target enrichment can be by any means known in the art. For example, the nucleic acid sample may be enriched by amplifying target sequences using target-specific primers. The target amplification can occur in a digital PCR format, using any methods or systems known in the art. The nucleic acid sample may be enriched by capture of target sequences onto an array immobilized thereon target-selective oligonucleotides. The nucleic acid sample may be enriched by hybridizing to target-selective oligonucleotides free in solution or on a solid support. The oligonucleotides may comprise a capture moiety which enables capture by a capture reagent. Capture moiety/capture reagent pairs are known in the art. In some embodiments the capture reagent is avidin, streptavidin, or neutravidin and the capture moiety is biotin. In another embodiment the capture moiety/capture reagent pair is digoxigenin/wheat germ agglutinin.

In some embodiments, the nucleic acid sample is not enriched for target polynucleotides, e.g., represents a whole genome.

In some embodiments, diseased circulating polynucleotides from the fluid sample are detected by the presence or absence of one or more genetic abnormalities associated with the disease. For instance, ctDNA (circulating tumor DNA) may be detected based on presence or absence of one or more cancer-associated genetic abnormalities. Many types of genetic abnormalities are known in the art and may include mutations to a chromosome and/or mutations to the genetic sequence. Many types of chromosomal abnormalities are known in the art and may include a structural abnormality (e.g., translocations, inversions, or insertions) or an atypical number of chromosomes (e.g., copy number variations such as deletions or duplications).

In the case of multiple myeloma, the diseased circulating polynucleotides may comprise one or more mutations in one or more genes selected from KRAS, NRAS, TP53, DIS3, FAM46C, BRAF, TRAF3, PRDM1, CYLD, RB1, ACTG1, IRF4, IDH1, INTS12, SP140, LTB, MAX, HIST1H1E, EGR1, FGFR3, FNDC3A, TNKS, BCL7A, RPL10, GCET2, RASA2, PLA2G2D, C9orf80, HIST1H3G, CDKN1B, RNF151, C17orf77, FAM153B, SLC24A1, OR1L8, USP50, CXCR4, KRTDAP, FBXO36, ROBO1, TGDS, SNX7, MPEG1, DHX32, RYR2, NFKBIA, FSIP2, SI, NECAB3, COASY, EIF4G2, ZFHX4, CCND1, LRRC16A, YTHDF2, PHOX2B, C15orf59, MOGAT3, EXOG GRIA2, C4orf43, CCDC144NL, CKM, OR1N2, PRIM2, OR1S2, NDUFAF3, C20orf112, HIST1H3H, and PNRC1. In some cases a genetic abnormality is one or more of KRAS (p.G12D), KRAS (p.Q61H), NRAS (p.G12D), BRAF (p.G469R), IRF4 (p.L116R), SLC24A1 (p.R686G), MPEG1 (p.G537E), and RYR2 (p.I784V). Such genetic abnormalities associated with multiple myeloma are described in US2018/0305766A1, which is hereby incorporated by reference in its entirety.

In some embodiments, the diseased circulating polynucleotides from the fluid sample are detected by next generation sequencing. The next generation sequencing may comprise sequencing of immunoglobulin gene segments. Exemplary next generation sequencing techniques are described in Kumar S et al. International Myeloma Working Group consensus criteria for response and minimal residual disease assessment in multiple myeloma. Lancet Oncol 2016; 17:e328-46, which is hereby incorporated by reference in its entirety.

Kits

Also provided herein is a kit, comprising a pharmaceutically acceptable dosage form of a mobilizing agent disclosed herein, and instructions for use.

In some embodiments, such kits comprise a carrier, package or container that is compartmentalized to receive one or more containers such as vials, tubes, and the like, each of the container(s) comprising one of the separate elements to be used in the method. The kit can comprise the container described above and one or more other containers comprising materials desirable from a commercial end user standpoint, including buffers, diluents, filters, and package inserts with instructions for use. In addition, a label can be provided on the container to indicate that the composition is used for a specific therapeutic application and can also indicate directions for either in vivo or in vitro use, such as those described above. Directions and or other information can also be included on an insert which is included with the kit.

Non-Transitory Computer Readable Medium

Also provided herein is a computer readable medium comprising computer executable instructions configured to implement any of the methods described herein. In various embodiments, the computer readable medium is a non-transitory computer readable medium. In some embodiments, the computer readable medium is a part of a computer system (e.g., a memory of a computer system). The computer readable medium can comprise computer executable instructions for, e.g., generating a report of a subject's MRD determination, prognosis, genetic profile of the one or more diseased cells or diseased polynucleotides obtained by a method disclosed herein, and optionally transmitting the report over a network.

Also provided herein is a computer system comprising a computer readable medium disclosed herein.

Systems

Also provided herein is a system for liquid biopsy yield enhancement (LBYE). In some embodiments, the system comprises one or more pharmaceutically acceptable dosage forms of a mobilizing agent disclosed herein (e.g., one or more dosage forms of plerixafor for administration to the subject). The system may further comprise reagents, devices, and/or kits for obtaining a fluid sample from a subject in need thereof (e.g., a fluid collection tube and optionally reagents for enhancing stability of the fluid sample). The system may further comprise one or more reagents, devices, and/or apparatuses for analyzing diseased cells or diseased polynucleotides (e.g., one or more reagents, devices, and/or apparatuses for multiparametric flow cytometry analysis, a sequencer, and the like).

Methods for MRD Detection

The methods described herein can be used for MRD detection in a subject. Such methods are particularly advantageous for the detection of MRD, because mobilization of diseased cells (e.g., tumor cells) and/or debris from diseased cells (e.g., ctDNA) enhances yield of the diseased cells and/or polynucleotides, thus enhancing sensitivity of the assay and reducing false negatives. Accordingly, in some embodiments, a detected presence of tumor cells or ctDNA in the fluid sample is indicative of MRD in the subject. Likewise, detected absence of tumor cells or ctDNA in the fluid sample is indicative of a true MRD absence in the subject. In some embodiments, the method further comprises administering a cancer therapeutic to the subject if MRD is detected.

Accordingly, provided herein is a method of detecting presence or absence of MRD in a subject in need thereof, comprising analyzing a fluid sample obtained from the subject or detecting one or more tumor cells or tumor DNA in a fluid sample obtained from the subject, according to a method described herein, wherein (i) presence of the one or more tumor cells or tumor DNA in the fluid sample indicates presence of MRD in the subject, and (ii) absence of the one or more tumor cells or tumor DNA in the fluid sample indicates absence of MRD in the subject.

In some embodiments of an MRD detection method, administration of the mobilizing agent, subsequent fluid sample collection, and analysis of the fluid sample is performed when the subject is determined to be in remission or suspected by a clinician to be in complete remission from cancer. In some embodiments of an MRD detection method, administration of the mobilizing agent, subsequent fluid sample collection, and analysis of the fluid sample is performed after the subject has concluded a course of disease therapy, e.g., a course of anticancer therapy. In some embodiments of an MRD detection method, administration of the mobilizing agent, subsequent fluid sample collection, and analysis of the fluid sample is performed after the subject's cancer is undetectable by conventional means. In some embodiments, administration of the mobilizing agent, subsequent fluid sample collection, and analysis of the fluid sample is performed after the subject has completed sufficient anticancer therapy as to render to cancer undetectable by conventional means such as microscopy, measurement of tumor markers, standard flow cytometry, biopsy, imaging studies (e.g., X-rays, CT scans, radionuclide scans, PET scans, MRI scans). Conventional means may include means known in the art such as, e.g., medical imaging, liquid biopsy without enhancement (by use of one or more mobilizing agents described herein), and solid tissue biopsy.

In some embodiments, presence of diseased cells or diseased polynucleotides in the fluid sample obtained according to an LBYE method disclosed herein indicates that the subject has MRD. In some embodiments, absence of diseased cells or diseased polynucleotides in the fluid sample obtained according to an LBYE method disclosed herein indicates lack of MRD in the subject, and provides a more accurate indication that the subject is in complete remission. Methods for detecting presence or absence of diseased cells in the fluid sample are disclosed supra. Methods for detecting presence or absence of diseased polynucleotides in the fluid sample are disclosed supra.

In some embodiments, the administration of the one or more mobilizing agents, the subsequent collection of the fluid sample, and the analysis of the fluid sample is performed once. In some embodiments, the administration of the one or more mobilizing agents, the subsequent collection of the fluid sample, and the analysis of the fluid sample is performed more than once (i.e.—at least two times). For example, if the initial LBYE method detects presence of MRD in the subject, the subject may be administered an additional course of anticancer therapy, and the LBYE method performed for detection of MRD after the subject has concluded the additional course of therapy. For other example, if the initial LBYE method detects absence of MRD, the LBYE method may be performed one or more subsequent times, in order to monitor the subject for MRD resurgence or relapse. In some embodiments, wherein the initial LBYE test detects absence of MRD, maintenance therapy may be administered to the subject. Maintenance therapy generally comprises administration of an anticancer agent in an amount effective to maintain a therapeutic benefit to the subject that was achieved via a therapeutic anticancer regimen, e.g., (1) inhibiting an increase in the number of cancer cells; (2) inhibiting an increase in tumor size; (3) inhibiting cancer cell infiltration into peripheral organs; (4) inhibiting tumor metastases; (5) relieving or reducing to some extent one or more of the symptoms associated with the disorder; and/or (6) inhibiting recurrence or relapse of the cancer. In some embodiments, the maintenance therapy comprises administration of the therapeutic anticancer regimen at a lower dosage scheme. In some embodiments, wherein the initial LBYE method was negative for MRD, disease therapy for the subject is terminated. In some embodiments wherein the initial LBYE test detects presence of MRD, maintenance therapy or standard therapy is administered to the subject. In some embodiments, the LBYE method is repeated at regular intervals for the monitoring of MRD resurgence or relapse. In some embodiments, the LBYE method is performed at a frequency of about once a month, one every 2 months, once every 3 months, once every 4 months, once every 6 months, once a year.

In some embodiments, a report of the determination of a subject's MRD status according to any of the methods disclosed herein is transmitted over a network.

Determination of Complete Remission

The MRD detection methods disclosed herein are particularly useful in certain embodiments, such as detection of MRD when the subject has been determined to be, or suspected of being, in complete remission. Accordingly, in some embodiments, administration of the mobilizing agent, subsequent fluid sample collection, and analysis of the fluid sample is performed when the subject is determined or suspected of being in remission from multiple myeloma.

In some embodiments, a subject is determined or suspected to be in remission when the subject has completed a course of anticancer therapy. For example, a subject may be expected to be in remission when the subject has undergone an autologous stem cell transplant (ASCT). In some embodiments, the subject is expected to be in remission one month, two months, three months, or more than three months after undergoing ASCT. In some embodiments, the subject is suspected of being in remission about 100 days after receiving ASCT.

In some embodiments, administration of the mobilizing agent, subsequent fluid sample collection, and analysis of the fluid sample is performed when the subject is determined or suspected of being in remission from multiple myeloma according to conventional criteria.

A skilled artisan, e.g., a clinician, may determine whether a subject with myeloma is expected to be in remission according to any conventional criteria known in the art. Exemplary embodiments of conventional criteria for determining whether a subject with myeloma is expected to be in remission are described in Kumar et al. (Lancet Oncology), which is hereby incorporated by reference in its entirety. In some embodiments, a subject with myeloma is determined or expected to be in remission according to conventional criteria when all of following conditions (1)-(6) are met: (1) no abnormal (clonal) plasma cells in the bone marrow, (2) disappearance of the original disease-specific monoclonal protein from blood and/or urine on immunofixation electrophoresis, (3) disappearance of all plasmacytomas (tumors), (4) lack of new bone lesions on one or more imaging studies (X-rays, CT scans, MRI scans, PET scan), (5) no disproportionate elevation of the involved (disease-specific) serum free light chain level, and (6) no concordant abnormal free light chain ratio in serum. For example, in some embodiments, disappearance of the original disease-specific monoclonal protein from blood and/or urine on immunofixation electrophoresis may be defined as remission according to conventional criteria. In some embodiments, a subject with myeloma is determined or expected to be in remission according to conventional criteria when the first two of conditions (1)-(6) are met. In some embodiments, a subject with myeloma is determined or expected to be in remission according to conventional criteria when the first three of conditions (1)-(6) are met. In some embodiments, a subject with myeloma is determined or expected to be in remission according to conventional criteria when the first four of conditions (1)-(6) are met. In some embodiments, a subject with myeloma is determined or expected to be in remission according to conventional criteria when the first five of conditions (1)-(6) are met. By way of example only, a subject with myeloma is determined or expected to be in remission according to conventional criteria when conditions (2)-(6) are met. In some embodiments, a subject with myeloma is determined or expected to be in remission according to conventional criteria when the second of conditions (1)-(6) is met ("serologic CR"). In the foregoing examples, the subject can be confirmed to be in complete remission when the LBYE method detects no CTC or ctDNA in the fluid sample of the subject. It is known that a minority of the malignant cell population in myeloma— usually the one most difficult to eliminate with therapy— does not secrete paraprotein (the abnormal protein easily detectable in the blood). LBYE is especially important to identify MRD in this situation—and can potentially change the current definition of CR in myeloma.

Bone lesions may be detectable by medical imaging, according to any method known in the art. The medical imaging may comprise skeletal radiography (e.g., X-ray), CT (including low-dose whole body CT), MRI, $^{18}$F-fluorodeoxyglucose (FDG) PET, and FDG-PET with CT (PET-CT). In some embodiments, a bone lesion is diagnosed by the presence of one or more sites of osteolytic bone destruction (≥5 mm in size) seen on CT (including low dose whole-body CT) or PET-CT. Such criteria are described in Rajkumar S et al., which is hereby incorporated by reference in its entirety.

Serum free light chain levels and ratios can be determined according to any method known in the art. The free light chain (FLC) assay measures the ratio of free κ and λ light immunoglobulin chains (unbound to immunoglobulin heavy chains) in the serum. The normal ratio for FLC-κ/λ is 0·26-1·65. Ratios outside the normal range, e.g., ratios of about 100 are used to indicate multiple myeloma. Such assays are described in Rajkumar S et al. International Myeloma Working Group updated criteria for the diagnosis of multiple myeloma. Lancet Oncol. 2014 November; 15(12):e538-48. doi: 10.1016/S1470-2045(14)70442-5, which is hereby incorporated by reference in its entirety.

Abnormal (clonal) plasma cells in a bone marrow sample of the subject can be detected according to any methods known in the art.

In some embodiments, abnormal plasma cells of the bone marrow are detected by core bone marrow biopsy with immunohistochemical staining with CD138 antibody. In some embodiments, abnormal plasma cells of the bone marrow are detected by counting cells on a marrow aspirate smear.

In some embodiments, abnormal plasma cells of the bone marrow are detected by flow cytometry of a bone marrow sample of the subject. In some embodiments, multiple myeloma cells in the bone marrow sample are detected by flow cytometry. The flow cytometry may comprise multiparametric flow cytometry. Such techniques can be used to distinguish multiple myeloma plasma cells from non-diseased plasma cells. Exemplary multiparameteric flow cytometry techniques are described in Kumar S et al. International Myeloma Working Group consensus criteria for response and minimal residual disease assessment in multiple myeloma. Lancet Oncol 2016; 17:e328-46, which is hereby incorporated by reference in its entirety. In some embodiments, the multiparametric flow cytometry comprises gating for any one or more of CD138, CD38, CD45, CD56, CD19, cytoplasmic κ and λ immunoglobulin light chains, CD20, CD27, CD28, CD81, CD117, CD200, CD54, CD229, CD319, and VS38c. In particular embodiments, the multiparametric flow cytometry comprises gating for any one or more of CD138, CD38, CD45, CD56, CD19, and cytoplasmic κ and λ immunoglobulin light chains. In other particular embodiments, the multiparametric flow cytometry comprises gating for CD19, CD45, CD56, CD81, CD27, CD117, and cytoplasmic κ and λ immunoglobulin light chains. In preferred embodiments, the multiparametric flow cytometry comprises gating for CD138. In some embodiments, wherein the subject had been previously treated with an anticancer therapy comprising a monoclonal antibody against CD38 or CD138, the multiparametric flow cytometry comprises gating for any one or more of CD54, CD229, CD319, and VS38c. Exemplary multiparametric flow cytometry techniques are described in Kumar S et al. International Myeloma Working Group consensus criteria for response and minimal residual disease assessment in multiple myeloma. Lancet Oncol 2016; 17:e328-46, which is hereby incorporated by reference in its entirety, in WO2017198879A1, which is hereby incorporated by reference in its entirety. Other exemplary multiparametric flow cytometry methods for detection of multiple myeloma MRD in bone marrow samples are described in Flores-Montero J, Sanoja-Flores L, Paiva B, et al. Next generation flow for highly sensitive and standardized detection of minimal residual disease in multiple myeloma. Leukemia 2017; 31:2094-2103, in Mishima Y et al., The Mutational Landscape of Circulating Tumor Cells in Multiple Myeloma, Cell Rep. 2017 Apr. 4; 19(1): 218-224. doi:10.1016/j.celrep.2017.03.025, and in US20180140664A1, which are hereby incorporated by reference in their entireties.

In some embodiments, determination of remission comprises use of ASO-qPCR to detect presence or absence of multiple myeloma cells in the bone marrow sample. Exemplary ASO-qPCR techniques are described in Kumar S et al. International Myeloma Working Group consensus criteria for response and minimal residual disease assessment in multiple myeloma. Lancet Oncol 2016; 17:e328-46, which is hereby incorporated by reference in its entirety.

In some embodiments, determination of remission comprises use of next generation sequencing to detect presence or absence of multiple myeloma cells in the bone marrow sample. The next generation sequencing may comprise sequencing of immunoglobulin gene segments. Exemplary next generation sequencing techniques are described in Kumar S et al. International Myeloma Working Group consensus criteria for response and minimal residual disease assessment in multiple myeloma. Lancet Oncol 2016; 17:e328-46, which is hereby incorporated by reference in its entirety.

Additional conventional factors which may be considered when determining whether a subject is in complete remission from multiple myeloma includes assessment of hypercalcaemia, assessment of renal insufficiency, and assessment of anemia. Such criteria are described in Rajkumar S et al. International Myeloma Working Group updated criteria for the diagnosis of multiple myeloma. Lancet Oncol. 2014 November; 15(12):e538-48. doi: 10.1016/S1470-2045(14) 70442-5, which is hereby incorporated by reference in its entirety.

Methods for Disease Prognosis

The methods described herein are also useful for disease prognosis in a subject in need thereof. Prognosis can include predicting the outcome of the subject's disease, chance of recovery from the disease, response to a course of therapy, or tracking the progression of the disease. Prognosis can also include determining a course of therapy for the subject, based, e.g., on genetic profile of a subject's diseased cell or diseased polynucleotide.

Accordingly, in some aspects provided herein is a method of prognosing a subject in need thereof, comprising genetically profiling one or more diseased cells or diseased circulating polynucleotides that have been obtained from a fluid sample obtained from the subject, the subject having been previously administered a mobilizing agent disclosed herein in an amount effective to stimulate release of the one or more diseased cells or diseased circulating polynucleotides into circulation, wherein the genetic profile is used in prognosis of the subject. In some embodiments, the method comprises administration of the mobilizing agent to the subject, collection of the fluid sample from the subject, and genetically profiling diseased cells or diseased polynucleotides released into the fluid sample.

In some embodiments of any of the prognostic methods disclosed herein, the subject is determined to have the disease. In some embodiments, the subject is determined to have cancer. In some embodiments, the subject is determined to not be in remission, or is suspected of harboring active disease.

In some embodiments, a report of the determination of a subject's prognosis according to any of the methods disclosed herein is transmitted over a network.

Methods for Disease Detection

The methods described herein are also useful for disease detection in a subject in need thereof. For example, the methods described herein are useful for detecting disease in the subject at very early stages of the disease, prior to when the disease would be detectable by otherwise conventional means.

Accordingly, provided herein is a method of detecting a disease in a subject, comprising detecting one or more diseased cells or disease-associated polynucleotides in a fluid sample obtained from a subject, wherein the subject was previously administered a cytokine or growth factor in an amount effective to stimulate release of the one or more diseased cells or disease-associated polynucleotides into circulation, and wherein the detection of the one or more diseased cells or disease-associated polynucleotides is indicative of the disease in the subject.

In some embodiments, the disease is cancer.

In some embodiments, the diseased cells comprise tumor cells. In some embodiments, the disease-associated polynucleotides are tumor-associated polynucleotides, e.g., tumor DNA.

Methods of Treatment

In some aspects, provided herein are methods of treatment. The method of treatment may comprise a method of treating cancer. In some embodiments, the method of treating cancer comprises administering at least one cancer therapeutic to the subject if one or more tumor cells or tumor DNA has been detected in a fluid sample obtained from the subject following administration of a mobilizing agent disclosed herein in an amount effective to stimulate release of the one or more tumor cells or tumor DNA into circulation of the subject. Exemplary anticancer therapeutics (cancer therapeutics) are disclosed herein. In some embodiments, the anticancer therapeutic comprises an HSC transplant. In some embodiments, the anticancer therapeutic comprises an autologous HSC transplant. In particular embodiments, the anticancer therapeutic does not comprise an autologous HSC transplantation. In some embodiments, the anticancer therapeutic comprises an allogeneic HSC transplant. In some embodiments, the anticancer intervention comprises immunotherapy (including but not limited to cell therapy such as CAR-T cells, immune activating agents such as checkpoint inhibitors, and various combinations thereof).

In some embodiments, methods of treatment comprise determining a mutational or genetic profile of one or more diseased cells or disease-associated polynucleotides obtained from a subject via LBYE, and administering an anticancer therapeutic to the subject based on the determined genetic profile.

Pharmaceutical Compositions

Methods for treatment are also encompassed by the present invention. Said methods of the invention include administering a therapeutically effective amount of a therapeutic, e.g., an anticancer drug to the subject. The therapeutic can be formulated in pharmaceutical compositions. These compositions can comprise, in addition to one or more active ingredients, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, intramuscular or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, Lactated Ringer's injection. Preservatives, stabilizers, buffers, antioxidants and/or other additives can be included, as required.

Whether it is a polypeptide, antibody, nucleic acid, small molecule or other pharmaceutically useful compound that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of the disease being treated. Prescription of treatment, e.g. decisions on dosage etc., is within the responsibility of the cancer specialist (hematologist or oncologist) or other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: LBYE for MRD Detection (Multiple Myeloma)

Human patients who have undergone an anticancer treatment for multiple myeloma are split into two experimental groups, an "LBYE" and "control group". Patients may be matched across experimental groups by age, sex, and other clinical factors, such as multiple myeloma burden or genetic profile of the multiple myeloma in the patient.

When in complete remission using conventional techniques after appropriate therapy, patients in the control group undergo a blood as well as bone marrow examination each of which is subjected to MRD detection/assay using the ClonoSEQ® technique (Adaptive Biotechnologies). A comparable "LBYE" experimental group is administered a single 20 mg dose of plerixafor or a variation thereof as described. About 12 hours after plerixafor administration, patients in the LBYE group undergo a blood draw. The blood samples are subjected to MRD assay using the ClonoSEQ® technique. Residual disease is detected in a greater number of patients in the LBYE group than in the control group, indicating successful mobilization of diseased cells in the patients undergoing LBYE sampling.

In another variation of the experiment, where myeloma patients serve as their own controls, patients undergo bone marrow examination after attaining complete remission. The marrow is subjected to MRD assay by ClonoSEQ®. After the marrow exam is done, each patient receives 20 mg plerixafor and the blood is sampled 12 hours later. Blood samples are subjected to MRD assay by ClonoSEQ®. A greater proportion of patients is found to be positive for MRD from the blood after the LBYE technique than the bone marrow. All or most patients positive for MRD from the bone marrow are positive for MRD from the blood after LBYE technique, whereas a number of patients who are negative for MRD from the bone marrow are positive from the blood after the LBYE technique.

Cell-free DNA (cfDNA) is isolated from patient plasma samples according to known methods.

The concentration of the isolated cfDNA from LBYE and control patients are determined. Patients in the LBYE group exhibit higher cfDNA concentrations than patients in the control group, indicating successful mobilization of diseased ctDNA in the patients undergoing LBYE sampling, and indicating improved sensitivity for detecting MRD utilizing the LBYE methods disclosed herein and indicating improved sensitivity for detecting MRD utilizing the LBYE methods disclosed herein.

The cfDNA is subjected to whole exome sequencing or targeted sequencing to determine mutational profile of the cfDNA sample. Mutational profile of the cfDNA sample is, in some cases, compared to mutational profile of multiple myeloma cells obtained from bone marrow sample from the same patient.

Example 2: Patient Follow Up Following LBYE for MRD Detection (Multiple Myeloma)

Human patients for which CTCs or ctDNA were detected by LBYE as described in Example 1 are administered a further course of anticancer treatment and monitored for relapse. The monitoring may comprise clinical assessment for relapse by any means known in the art. In some cases, the patients undergo further LBYE sampling and analysis, according to the methods described in Example 1.

Human patients for which CTCs or ctDNA were not detected by LBYE as described in Example 1 are not administered a further course of anticancer treatment. Such patients are further monitored for presence or absence of CTCs and/or ctDNA at regular intervals using the methods described in Example 1. The clinician determines the frequency and duration of the monitoring by the methods described in Example 1, which can range from e.g., once a month, once every two months, once every three months, once every four months, once every 6 months, once a year, for 1-10 years, 1-5 years, 1-3 years, or any of the subranges within 1-10 years.

Example 3: LBYE for Active Disease Prognosis (Multiple Myeloma)

Human patients who are diagnosed with multiple myeloma are split into two experimental groups, an "LBYE" group and a "control group". Patients may be matched across experimental groups by age, sex, and other clinical factors, such as multiple myeloma burden or genetic profile of the multiple myeloma in the patient.

Patients in the "LBYE" experimental group are administered a single dose of 20 mg plerixafor and undergo blood sampling 12 hours later. This sample is analyzed for the presence of various mutations and genetic variations known to influence prognosis in myeloma. Patients in the control group undergo a bone marrow examination that is subjected to similar testing. Patients in the LBYE group show a greater frequency and breadth of abnormalities than those in the control group. In a variation on the above experiment, the LBYE group patients undergo a bone marrow examination which is subjected to appropriate testing. The final result of the LBYE group is the sum total of findings from the blood and the marrow of each patient—and shows greater amount of relevant information than the control group subjected to bone marrow sampling alone.

In another variation on the experiment, the LBYE group's marrow and blood sample are pooled and analyzed in a single assay to make the test more cost-effective. Blood samples are separated a plasma fraction and cellular fractions. In yet another variation, only an LBYE group is studied and greater information found in the blood after LBYE compared to the bone marrow of the same patient. The cell fraction is analyzed for the presence of multiple myeloma CTCs by multiparametric flow cytometry according to methods described herein. Multiple myeloma CTCs are genetically profiled, e.g., by sequencing to determine the mutational profile of the CTCs. Mutational profile of the CTC sample is, in some cases, compared to mutational profile of multiple myeloma cells obtained from bone marrow sample from the same patient.

In some cases, cell-free DNA (cfDNA) is isolated from patient plasma samples according to known methods and genetically profiled, e.g., by sequencing. Mutational profile of the cfDNA sample is, in some cases, compared to mutational profile of multiple myeloma cells obtained from bone marrow sample from the same patient.

The mutational profile of the CTCs and/or cfDNA is used by a clinician for the patient's prognosis and treatment choice.

In some cases, the genetic profile of the CTCs and/or cfDNA is further monitored at regular intervals using the methods described in this Example. The clinician determines the frequency and duration of the monitoring by the methods described in this example, which can range from, e.g., once a month, once every two months, once every three months, once every four months, once every 6 months, once a year, for 1-10 years, 1-5 years, 1-3 years, or any of the subranges within 1-10 years.

Example 4 LBYE for MRD Detection (Lymphoma)

Human patients who have undergone an anticancer treatment for lymphoma are split into two experimental groups, an "LBYE" and "control group." Patients may be matched across experimental groups by age, sex, and other clinical factors, such as lymphoma burden or genetic profile of the lymphoma in the patient.

When in complete remission using conventional techniques after appropriate therapy, patients in the control group undergo a blood as well as bone marrow examination each of which is subjected to MRD detection/assay using any of the techniques described earlier (including but not limited to flow cytometry, sequencing, etc.) A comparable "LBYE" experimental group is administered a single 20 mg dose of plerixafor or a variation thereof as described. About 12 hours after plerixafor administration, patients in the LBYE group undergo a blood draw. The blood samples are subjected to MRD assay. Residual disease is detected in a greater number of patients in the LBYE group than in the control group, indicating successful mobilization of diseased cells in the patients undergoing LBYE sampling.

In another variation of the experiment, where lymphoma patients serve as their own controls, patients undergo blood sampling after attaining complete remission. The blood is subjected to MRD assay. After the blood test is done, each patient receives 20 mg plerixafor and the blood is sampled 12 hours later. These blood samples are subjected to MRD assay by the same technique. A greater proportion of patients is found to be positive for MRD from the blood after the LBYE technique than the non-LBYE blood sample.

Cell-free DNA (cfDNA) is isolated from patient plasma samples according to known methods.

The concentration of the isolated cfDNA from LBYE and control patients are determined. In the second experiment, where patients serve as their own controls, even amongst patients exhibiting the presence of cfDNA (i.e. positive for MRD), the concentration/amount of cfDNA is higher after LBYE indicating successful mobilization of diseased ctDNA in the patients undergoing LBYE sampling, and indicating improved sensitivity for detecting MRD utilizing the LBYE methods disclosed herein and indicating improved sensitivity for detecting MRD utilizing the LBYE methods disclosed herein.

The cfDNA is subjected to whole exome sequencing or targeted sequencing to determine mutational profile of the cfDNA sample. Mutational profile of the cfDNA sample is, in some cases, compared to mutational profile of lymphoma cells obtained from bone marrow sample from the same patient.

Example 5: Patient Follow Up Following LBYE for MRD Detection (Lymphoma)

Human patients for which CTCs or ctDNA were detected by LBYE as described in Example 1 are administered a further course of anticancer treatment and monitored for relapse. The monitoring may comprise clinical assessment for relapse by any means known in the art. In some cases, the patients undergo further LBYE sampling and analysis, according to the methods described in Example 1.

Human patients for which CTCs or ctDNA were not detected by LBYE as described in Example 1 are not administered a further course of anticancer treatment. Such patients are further monitored for presence or absence of CTCs and/or ctDNA at regular intervals using the methods described in Example 1. The clinician determines the frequency and duration of the monitoring by the methods described in Example 1, which can range from e.g., once a month, once every two months, once every three months, once every four months, once every 6 months, once a year, for 1-10 years, 1-5 years, 1-3 years, or any of the subranges within 1-10 years.

Example 6: LBYE for Active Disease Prognosis (Lymphoma)

Human patients who are diagnosed with lymphoma are split into two experimental groups, an "LBYE" group and a "control group." Patients may be matched across experimental groups by age, sex, and other clinical factors, such as lymphoma burden or genetic profile of the lymphoma in the patient.

Patients in the "LBYE" experimental group are administered a single dose of 20 mg plerixafor and undergo blood sampling 12 hours later. This sample is analyzed for the presence of various mutations and genetic variations known to influence prognosis in myeloma. Patients in the control group undergo a bone marrow examination that is subjected to similar testing. Patients in the LBYE group show a greater frequency and breadth of abnormalities than those in the control group. In a variation on the above experiment, the LBYE group patients undergo a bone marrow examination which is subjected to appropriate testing. The final result of the LBYE group is the sum total of findings from the blood and the marrow of each patient—and shows greater amount of relevant information than the control group subjected to bone marrow sampling alone.

In another variation on the experiment, the LBYE group's marrow and blood sample are pooled and analyzed in a single assay to make the test more cost-effective. In yet another variation, only an LBYE group is studied and grater information found in the blood after LBYE compared to the bone marrow of the same patient. The mononuclear cell fraction is analyzed for the presence of lymphoma CTCs by multiparametric flow cytometry according to methods described herein. Lymphoma CTCs are genetically profiled, e.g., by sequencing to determine the mutational profile of the CTCs. Mutational profile of the CTC sample is, in some cases, compared to mutational profile of lymphoma cells obtained from bone marrow sample from the same patient.

In some cases, cell-free DNA (cfDNA) is isolated from patient plasma samples according to known methods and genetically profiled, e.g., by sequencing. Mutational profile of the cfDNA sample is, in some cases, compared to mutational profile of lymphoma cells obtained from bone marrow sample from the same patient.

The mutational profile of the CTCs and/or cfDNA is used by a clinician for the patient's prognosis and treatment choice.

In some cases, the genetic profile of the CTCs and/or cfDNA is further monitored at regular intervals using the methods described in this Example. The clinician determines the frequency and duration of the monitoring by the methods described in this example, which can range from, e.g., once a month, once every two months, once every three months, once every four months, once every 6 months, once a year, for 1-10 years, 1-5 years, 1-3 years, or any of the subranges within 1-10 years.

Example 7: LBYE for MRD Detection (Solid Tumor)

Human patients who have undergone an anticancer treatment for a specific solid tumor (e.g. lung cancer, breast cancer, colon cancer, amongst others) are split into two experimental groups, an "LBYE" and "control group." Patients may be matched across experimental groups by age, sex, and other clinical factors, such as solid tumor burden or genetic profile of the solid tumor in the patient.

When in complete remission using conventional techniques after appropriate therapy, patients in the control group undergo a blood examination each of which is subjected to MRD detection/assay using an appropriate assay (e.g. The Guardant 360 liquid biopsy or the Tempus XF liquid biopsy). A comparable "LBYE" experimental group is administered a single 20 mg dose of plerixafor or a variation thereof as described. About 12 hours after plerixafor administration, patients in the LBYE group undergo a blood draw. The blood samples are subjected to the same MRD assay. Residual disease is detected in a greater number of patients in the LBYE group than in the control group, indicating successful mobilization of diseased cells in the patients undergoing LBYE sampling.

In another variation of the experiment, where cancer patients serve as their own controls, patients undergo blood examination after attaining complete remission. Afterwards, each patient receives 20 mg plerixafor and the blood is sampled 12 hours later. Both samples are subjected to MRD assay. A greater proportion of patients is found to be positive for MRD from the blood sample obtained after plerixafor administration, as compared to the pre-plerixafor blood sample.

Cell-free DNA (cfDNA) is isolated from patient plasma samples according to known methods.

The concentration of the isolated cfDNA from LBYE and control patients are determined. Patients in the LBYE group exhibit higher cfDNA concentrations than patients in the control group, indicating successful mobilization of diseased ctDNA in the patients undergoing LBYE sampling, and indicating improved sensitivity for detecting MRD utilizing the LBYE methods disclosed herein and indicating improved sensitivity for detecting MRD utilizing the LBYE methods disclosed herein.

The cfDNA is subjected to whole exome sequencing or targeted sequencing to determine mutational profile of the cfDNA sample. Mutational profile of the cfDNA sample is, in some cases, compared to mutational profile of solid tumor cells obtained from the solid tumor sample from the same patient.

Example 8: Patient Follow Up Following LBYE for MRD Detection (Solid Tumor)

Human patients for which CTCs or ctDNA were detected by LBYE as described in Example 1 are administered a further course of anticancer treatment and monitored for relapse. The monitoring may comprise clinical assessment for relapse by any means known in the art. In some cases, the patients undergo further LBYE sampling and analysis, according to the methods described in Example 1.

Human patients for which CTCs or ctDNA were not detected by LBYE as described in Example 1 are not administered a further course of anticancer treatment. Such patients are further monitored for presence or absence of CTCs and/or ctDNA at regular intervals using the methods described in Example 1. The clinician determines the frequency and duration of the monitoring by the methods described in Example 1, which can range from e.g., once a month, once every two months, once every three months, once every four months, once every 6 months, once a year, for 1-10 years, 1-5 years, 1-3 years, or any of the subranges within 1-10 years.

Example 9: LBYE for Active Disease Prognosis (Solid Tumor)

Human patients who are diagnosed with one or more solid tumors are split into two experimental groups, an "LBYE" group and a "control group." Patients may be matched across experimental groups by age, sex, and other clinical factors, such as solid tumor burden or genetic profile of the solid tumor in the patient.

Patients in the "LBYE" experimental group are administered a single dose of 20 mg plerixafor and undergo blood sampling 12 hours later. This sample is analyzed for the presence of various mutations and genetic variations known to influence prognosis in myeloma. Patients in the control group undergo a solid tumor examination that is subjected to similar testing. Patients in the LBYE group show a greater frequency and breadth of abnormalities than those in the control group. In a variation on the above experiment, the LBYE group patients undergo a solid tumor examination which is subjected to appropriate testing. The final result of the LBYE group is the sum total of findings from the blood and the marrow of each patient—and shows greater amount of relevant information than the control group subjected to solid tumor sampling alone.

In another variation on the experiment, the LBYE group's tumor and blood samples are pooled and analyzed in a single assay to make the test more cost-effective. In yet another variation, only an LBYE group is studied and greater information found in the blood after LBYE compared to the solid tumor of the same patient. The mononuclear cell fraction is analyzed for the presence of solid tumor CTCs by multiparametric flow cytometry according to methods described herein. Solid tumor CTCs are genetically profiled, e.g., by sequencing to determine the mutational profile of the CTCs. Mutational profile of the CTC sample is, in some cases, compared to mutational profile of solid tumor cells obtained from solid tumor sample from the same patient.

In some cases, cell-free DNA (cfDNA) is isolated from patient plasma samples according to known methods and genetically profiled, e.g., by sequencing. Mutational profile of the cfDNA sample is, in some cases, compared to mutational profile of solid tumor cells obtained from solid tumor sample from the same patient.

The mutational profile of the CTCs and/or cfDNA is used by a clinician for the patient's prognosis and treatment choice.

In some cases, the genetic profile of the CTCs and/or cfDNA is further monitored at regular intervals using the methods described in this Example. The clinician determines the frequency and duration of the monitoring by the methods described in this example, which can range from, e.g., once a month, once every two months, once every three months, once every four months, once every 6 months, once a year, for 1-10 years, 1-5 years, 1-3 years, or any of the subranges within 1-10 years.

Example 10: LBYE for Screening Healthy Individuals

Individuals who are not known to have cancer undergo liquid biopsy as a screening tool. An unsuspected malignancy may be detected in a small proportion of such subjects. The same set of subjects undergoes screening after the LBYE technique. An unsuspected/undiagnosed malignancy is found in a greater proportion of subjects.

While the invention has been particularly shown and described with reference to a preferred embodiment and various alternate embodiments, it will be understood by persons skilled in the relevant art that various changes in form and details can be made therein without departing from the spirit and scope of the invention.

All references issued patents and patent applications cited within the body of the instant specification are hereby incorporated by reference in their entirety, for all purposes.

REFERENCES CITED

Fricker S P. Physiology and pharmacology of plerixafor. Transfus Med Hemother 2013; 40:237-45.

Kumar S et al. International Myeloma Working Group consensus criteria for response and minimal residual disease assessment in multiple myeloma. Lancet Oncol 2016; 17:e328-46.

Landgren O et al. New developments in diagnosis, prognosis, and assessment of response in multiple myeloma. Clin Cancer Res 2016; 22:5428-33.

Liu M C et al. Genome-wide cell-free DNA (cfDNA) methylation signatures and effect on tissue of origin (TOO) performance. J Clin Oncol 2019; 37 (suppl):3049.

Merker et al. Circulating tumor DNA analysis in patients with cancer: American Society of Clinical Oncology and College of American Pathologists joint review. J Clin Oncol 2018; 36:1631-41.

Pantel K et al. Liquid biopsy and minimal residual disease—latest advances and implications for cure. Nat Rev Clin Oncol 2019; 16:409-24.

Waldschmidt J M et al. Comprehensive characterization of circulating and bone marrow-derived multiple myeloma cells at minimal residual disease. Semin Hematol 2018; 55:33-7.

Zhao, Hongli et al. "CXCR4 over-expression and survival in cancer: a system review and meta-analysis." *Oncotarget* vol. 6, 7 (2015): 5022-40. doi:10.18632/oncotarget.3217

Rajkumar S et al. International Myeloma Working Group updated criteria for the diagnosis of multiple myeloma. Lancet Oncol. 2014 November; 15(12):e538-48. doi: 10.1016/S1470-2045(14)70442-5.

Flores-Montero J, Sanoja-Flores L, Paiva B, et al. Next generation flow for highly sensitive and standardized detection of minimal residual disease in multiple myeloma. Leukemia 2017; 31:2094-2103.

Harouaka, Ramdane A et al. "Circulating tumor cell enrichment based on physical properties." *Journal of laboratory automation* vol. 18, 6 (2013): 455-68. doi:10.1177/2211068213494391

Mishima Y et al., The Mutational Landscape of Circulating Tumor Cells in Multiple Myeloma, Cell Rep. 2017 Apr. 4; 19(1): 218-224. doi:10.1016/j.celrep.2017.03.025

Rasche L et al. Spatial genomic heterogeneity in multiple myeloma revealed by multi-region sequencing. Nat Commun 2017; 8: Article number 268.

Mithraprabhu S et al. Circulating tumour DNA analysis demonstrates spatial mutational heterogeneity that coincides with disease relapse in myeloma. Leukemia 2017; 31:1695-705.

US2018/0140664A1.

US2018/0305766A1.

WO2017/198879A1.

Debnath et al., Small molecule inhibitors of CXCR4, Theranostics. 2013; 3(1):47-75.

Lapierre V et al., Ancestim (r-metHuSCF) plus filgrastim and/or chemotherapy for mobilization of blood progenitors in 513 poorly mobilizing cancer patients: the French compassionate experience, Bone Marrow Transplantation (2011) 46:936-942.

Singhal et al. (Blood 2009) The relationship between the serum free light chain assay and serum immunofixation electrophoresis, and the definition of concordant and discordant free light chain ratios, Blood, Jul. 2, 2009, 114(1):38-39.

The invention claimed is:

1. A method of determining presence or absence of one or more tumor cells or tumor DNA in a fluid sample obtained from a subject, wherein:
   the subject is a human
   that has not been diagnosed to have a tumor, and
   the tumor is a solid tumor and is not lymphoma,
   said method comprising:
   a. administering to the subject plerixafor in an amount effective to stimulate release of the one or more tumor cells or tumor DNA into circulation;
   b. obtaining the fluid sample from the subject after administering plerixafor to the subject; and
   c. determining presence or absence of one or more tumor cells or tumor DNA in the fluid sample.

2. The method of claim 1, further comprising administering at least one cancer therapeutic to a subject determined to have one or more tumor cells or tumor DNA in the fluid sample.

3. The method of claim 2, wherein the cancer therapeutic is selected from 5-Fluorouracil, 6-Mercaptopurine, 6-Thioguanine, Abemaciclib, Abiraterone Acetate, Acalabrutinib, Ado-Trastuzumab Emtansine, Afatinib Dimaleate, Aldesleukin, Alectinib, Alemtuzumab, Alpelisib, Amifostine, Aminolevulinic Acid Hydrochloride, Anastrozole, Apalutamide, Arsenic Trioxide, L-Asparaginase, Atezolizumab, Avelumab, Axitinib, Azacitidine, Belinostat, Bendamustine Hydrochloride, Bevacizumab, Bexarotene, Bicalutamide, Binimetinib, Bleomycin Sulfate, Blinatumomab, Bortezomib, Bosutinib, Brentuximab Vedotin, Brigatinib, Busulfan, Cabazitaxel, Cabozantinib-S-Malate, Calaspargase Pegol-mknl, Capecitabine, Caplacizumab-yhdp, Carboplatin, Carfilzomib, Carmustine, Carmustine Implant, Cemiplimab-rwlc, Ceritinib, Cetuximab, Chlorambucil, Cisplatin, Cladribine, Clofarabine, Cobimetinib, Copanlisib Hydrochloride, Corticosteroids, Crizotinib, Cyclophosphamide, Cytarabine, Dabrafenib Mesylate, Dacarbazine, Dacomitinib, Dactinomycin, Daratumumab, Darolutamide, Dasatinib, Daunorubicin Hydrochloride, Daunorubicin Hydrochloride and Cytarabine Liposome, Decitabine, Defibrotide Sodium, Degarelix, Denileukin Diftitox, Denosumab, Dexamethasone, Dexamethasone, Dexrazoxane Hydrochloride, Dinutuximab, Docetaxel, Doxorubicin Hydrochloride, Doxorubicin Hydrochloride Liposome, Durvalumab, Duvelisib, Elotuzumab, Eltrombopag Olamine, Emapalumab-lzsg, Enasidenib Mesylate, Encorafenib, Entrectinib, Enzalutamide, Epirubicin Hydrochloride, Erdafitinib, Eribulin Mesylate, Erlotinib Hydrochloride, Etoposide, Etoposide Phosphate, Everolimus, Exemestane, Fedratinib Hydrochloride, Fludarabine Phosphate, Flutamide, Fostamatinib Disodium, Fulvestrant, Gefitinib, Gemcitabine Hydrochloride, Gemtuzumab Ozogamicin, Gilteritinib Fumarate, Glasdegib Maleate, Glucarpidase, Goserelin Acetate, Hydroxyurea, Ibritumomab Tiuxetan, Ibrutinib, Idarubicin Hydrochloride, Idelalisib, Ifosfamide, Imatinib Mesylate, Imiquimod, Inotuzumab Ozogamicin, Interferon Alfa-2b, Recombinant, Iobenguane I 131, Ipilimumab, Irinotecan Hydrochloride, Irinotecan Hydrochloride Liposome, Ivosidenib, Ixabepilone, Ixazomib Citrate, Lanreotide Acetate, Lapatinib Ditosylate, Larotrectinib Sulfate, Lenalidomide, Lenvatinib Mesylate, Letrozole, Leuprolide Acetate, Lomustine, Lorlatinib, Mechlorethamine Hydrochloride, Megestrol Acetate, Melphalan, Methotrexate, Methylnaltrexone Bromide, Methylprednisolone, Midostaurin, Mitomycin C, Mitoxantrone Hydrochloride, Mogamulizumab-kpkc, Moxetumomab Pasudotox-tdfk, Necitumumab, Nelarabine, Neratinib Maleate, Netupitant and Palonosetron Hydrochloride, Nilotinib, Nilutamide, Niraparib Tosylate Monohydrate, Nivolumab, Obinutuzumab, Ofatumumab, Olaparib, Omacetaxine Mepesuccinate, Osimertinib Mesylate, Oxaliplatin, Paclitaxel, Paclitaxel Albumin-stabilized Nanoparticle Formulation, Palbociclib, Palifermin, Panitumumab, Panobinostat, Pazopanib Hydrochloride, Pegaspargase, Peginterferon Alfa-2b, Pembrolizumab, Pemetrexed Disodium, Pertuzumab, Polatuzumab Vedotin-piiq, Pomalidomide, Ponatinib Hydrochloride, Pralatrexate, Prednisone, Procarbazine Hydrochloride, Propranolol Hydrochloride, Raloxifene Hydrochloride, Ramucirumab, Ravulizumab-cwvz, Recombinant Interferon Alfa-2b, Regorafenib, Ribociclib, Rituximab, Rituximab and Hyaluronidase Human, Rolapitant Hydrochloride, Romidepsin, Romiplostim, Rucaparib Camsylate, Ruxolitinib Phosphate, Selinexor, Siltuximab, Sonidegib, Sorafenib Tosylate, Sunitinib Malate, Tagraxofusp-erzs, Talazoparib Tosylate, Tamoxifen Citrate, Temozolomide, Temsirolimus, Thalidomide, Thiotepa, Tocilizumab, Topotecan Hydrochloride, Toremifene, Trabectedin, Trametinib, Trastuzumab, Trastuzumab and Hyaluronidase-oysk, Trifluridine and Tipiracil Hydrochloride, Uridine Triacetate, Valrubicin, Vandetanib, Vemurafenib, Venetoclax, Vinblastine Sulfate, Vincristine Sulfate, Vincristine Sulfate Liposome, Vinorelbine Tartrate, Vismodegib, Vorinostat, Zanubrutinib, and Ziv-Aflibercept.

4. The method of claim 2, comprising administering 1 μg-1 g of the cancer therapeutic to the subject.

5. The method of claim 1, wherein the fluid sample is a blood sample.

6. The method of claim 5, wherein the blood sample is a plasma or serum sample.

7. The method of claim 5, wherein the blood sample is a whole blood sample or a cellular fraction of a whole blood sample.

8. The method of claim 1, comprising administering 0.1-0.4 mg/kg plerixafor or 10-25 mg plerixafor to the subject.

9. The method of claim 8, comprising administering about 0.24 mg/kg or about mg plerixafor to the subject.

10. The method of claim 8, comprising administering about 0.16 mg/kg or about 13 mg plerixafor to the subject.

11. The method of claim 1, comprising administering plerixafor subcutaneously, intramuscularly, intravenously, or by inhalation.

12. The method of claim 11, comprising administering plerixafor by subcutaneous injection.

13. The method of claim 1, wherein the plerixafor is administered daily for 1-4 days.

14. The method of claim 1, wherein the plerixafor is administered once prior to obtaining the fluid sample from the subject.

15. The method of claim 1, wherein the plerixafor is administered 6-48 hours prior to obtaining the fluid sample.

16. The method of claim 15, wherein the plerixafor is administered about 11 hours prior to obtaining the fluid sample.

17. The method of claim 1, wherein the steps a, b, and c are performed once.

18. The method claim 1, wherein the steps a, b, and c are performed at least two times.

19. The method of claim 1, wherein the tumor is known to express CXCR4.

20. The method of claim 1, wherein the tumor is selected from adrenal cancer, anal cancer, bile duct cancer, bladder cancer, bone cancer, cancer of the brain or central nervous system, basal cell skin cancer, breast cancer, cervical cancer, colorectal cancer, endometrial cancer, esophageal cancer, eye cancer, gallbladder cancer, gastrointestinal carcinoid tumors, gastrointestinal stromal tumor, gastric cancer, glioma, glioblastoma, head and neck cancer, Kaposi sarcoma, kidney cancer, laryngeal and hypopharyngeal cancer, liver cancer, melanoma, prostate cancer, lung cancer, malignant mesothelioma, merkel cell carcinoma, metastatic urothelial carcinoma, myelodysplastic syndrome, nasal cavity and paranasal sinus cancer, nasopharyngeal cancer, neuroendocrine cancer, neuroblastoma, oral cavity and oropharyngeal cancer, osteosarcoma, ovarian cancer, pancreatic cancer, penile cancer, pituitary tumors, renal cancer, retinoblastoma, hematological malignancy, rhabdomyosarcoma, salivary gland cancer, sarcoma, squamous cell skin cancer, small intestine cancer, stomach cancer, testicular cancer, thymus cancer, thyroid cancer, uterine cancer, and vaginal cancer.

21. The method of claim 20, wherein the cancer is selected from breast cancer, colorectal cancer, esophageal cancer, head and neck cancer, renal cancer, lung cancer, gynecologic cancer, liver cancer, prostate cancer, and gallbladder cancer.

22. The method of claim 1, wherein the one or more tumor cells or tumor DNA is released into circulation from a non-blood compartment.

23. The method of claim 1, wherein the presence or absence of one or more tumor cells or tumor DNA in the fluid sample is determined by flow cytometry.

24. The method of claim 23, wherein the flow cytometry comprises multiparameter flow cytometry.

25. The method of claim 24, wherein the multiparametric flow cytometry comprises gating for any one or more of CD138, CD38, CD45, CD56, CD19, cytoplasmic κ and λ immunoglobulin light chains, CD20, CD27, CD28, CD81, CD117, CD200, CD54, CD229, CD319, and VS38c.

26. The method of claim 1, wherein the presence or absence of one or more tumor cells or tumor DNA in the fluid sample is determined by sequence analysis.

27. The method of claim 26, wherein the sequence analysis comprises PCR.

28. The method of claim 26, wherein the sequence analysis comprises sequencing.

29. The method of claim 28, wherein the sequencing comprises deep sequencing.

30. The method of claim 1, wherein the presence or absence of one or more tumor cells or tumor DNA in the fluid sample is determined by an assay with a sensitivity of at least 1 in 100,000 cells.

* * * * *